US012543783B2

(12) United States Patent
Fujiki et al.

(10) Patent No.: US 12,543,783 B2
(45) Date of Patent: Feb. 10, 2026

(54) INHALATION DEVICE, METHOD, AND PROGRAM

(71) Applicant: Japan Tobacco Inc., Tokyo (JP)

(72) Inventors: Takashi Fujiki, Tokyo (JP); Tatsunari Aoyama, Tokyo (JP); Hiroshi Kawanago, Tokyo (JP); Ryo Yoshida, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 447 days.

(21) Appl. No.: 18/073,940

(22) Filed: Dec. 2, 2022

(65) Prior Publication Data

US 2023/0107955 A1 Apr. 6, 2023

Related U.S. Application Data

(63) Continuation of application No. PCT/JP2020/039099, filed on Oct. 16, 2020.

(51) Int. Cl.

*A24F 40/40* (2020.01)
*A24F 40/51* (2020.01)

(Continued)

(52) U.S. Cl.

CPC .............. *A24F 40/40* (2020.01); *A24F 40/51* (2020.01); *A24F 40/60* (2020.01); *A61M 11/042* (2014.02);

(Continued)

(58) Field of Classification Search

None

See application file for complete search history.

(56) References Cited

U.S. PATENT DOCUMENTS

2005/0109354 A1* 5/2005 Draghetti ................. A24C 5/39 131/108
2010/0163063 A1 7/2010 Fernando et al.

(Continued)

FOREIGN PATENT DOCUMENTS

CN 110693092 A 1/2020
JP 2011-34904 A 2/2011

(Continued)

OTHER PUBLICATIONS

International Search Report (PCT/ISA/210), issued in PCT/JP2020/039098, dated Dec. 28, 2020.

(Continued)

*Primary Examiner* — Philip Y Louie
*Assistant Examiner* — Nicole A Szumigalski
(74) *Attorney, Agent, or Firm* — Birch, Stewart, Kolasch & Birch, LLP

(57) ABSTRACT

The present invention provides an inhalation device with which it is possible to improve usability and promote users' safety and satisfaction with the inhalation device. An inhalation device according to the present invention is provided with a first member and a second member which is configured to be capable of being attached to and detached from the first member. This inhalation device includes: an active functional part which is provided to the first member; a passive functional part which is provided to the second member and which is capable of changing the state thereof according to the working of the active functional part; a sensor part which is provided to the first member and which detects a changed state of the passive functional part; and a control part which, on the basis of the detected state, determines whether the second member has been attached to the first member.

9 Claims, 10 Drawing Sheets

(51) Int. Cl.

| | |
|---|---|
| ***A24F 40/60*** | (2020.01) |
| ***A61M 11/04*** | (2006.01) |
| ***G01D 5/14*** | (2006.01) |

(52) U.S. Cl.

CPC ..... *G01D 5/142* (2013.01); *A61M 2205/3317* (2013.01)

(56) References Cited

U.S. PATENT DOCUMENTS

| | | | |
|---|---|---|---|
| 2013/0091435 A1 | 4/2013 | Im et al. | |
| 2014/0196736 A1 | 7/2014 | Fernando et al. | |
| 2018/0020727 A1 | 1/2018 | Hoffman et al. | |
| 2018/0094828 A1 | 4/2018 | Komiya et al. | |
| 2020/0345960 A1* | 11/2020 | Begin | A24F 40/40 |
| 2021/0195961 A1 | 7/2021 | Marubashi et al. | |
| 2022/0095684 A1* | 3/2022 | Ferrie | A46B 15/0055 |
| 2022/0346437 A1* | 11/2022 | Loeb | A24C 5/34 |

FOREIGN PATENT DOCUMENTS

| | | |
|---|---|---|
| JP | 2011-59194 A | 3/2011 |
| JP | 2012-513750 A | 6/2012 |
| JP | 2013-84249 A | 5/2013 |
| JP | 2015-512262 | 4/2015 |
| JP | 2017-512459 A | 5/2017 |
| JP | 2019-526240 A | 9/2019 |
| WO | WO 2013/148610 A1 | 10/2013 |
| WO | WO 2015/120124 A1 | 8/2015 |
| WO | WO 2018/135863 A1 | 9/2016 |
| WO | WO 2018/194882 A1 | 12/2016 |
| WO | WO 2019/084161 A1 | 5/2019 |
| WO | WO 2019/185747 A1 | 10/2019 |
| WO | WO 2020059049 A1 | 3/2020 |
| WO | WO 2020/182747 A1 | 9/2020 |
| WO | WO 2022/078904 A1 | 4/2022 |

OTHER PUBLICATIONS

International Search Report (PCT/ISA/210), issued in PCT/JP2020/039099, dated Dec. 28, 2020.

Extended European Search Report for European Application No. 20957726.1, dated Jun. 20, 2024.

Japanese Office Action for Japanese Application No. 2023-038406, dated Jun. 1, 2023, with English translation.

Japanese Office Action for Japanese Application No. 2024-004406, dated Apr. 15, 2024, with English translation.

U.S. Appl. No. 17/975,318, filed Oct. 27, 2022.

Japanese Office Action dated Oct. 17, 2023 for Application No. 2023-038406 with English translation.

European Communication pursuant to Article 94(3) EPC for European Application No. 20 957 726.1, dated Jul. 18, 2025.

Korean Office Action for Korean Application No. 10-2022-7041339, dated Sep. 1, 2025, with English translation.

* cited by examiner

INHALATION DEVICE, METHOD, AND PROGRAM

CROSS REFERENCE TO RELATED APPLICATIONS

The present application is a continuation application of International Application No. PCT/JP2020/039099, filed on Oct. 16, 2020, which is hereby expressly incorporated by reference into the present application.

TECHNICAL FIELD

The present disclosure relates to an inhaler, a method, and a program.

BACKGROUND ART

As one of electronic devices, an inhaler which generates an inhaled component, such as flavor-added aerosol, has been known. Usually, in such an inhaler, a flavor-added inhalation article is attached thereto, and a suction action is performed by a user.

In such inhalers, some inhalers which can be customized to fit it to preference of respective users have been known. Specifically, there is an inhaler which allows a user to set an operation mode of the inhaler, for providing operability and experience that fits preference of the user. In addition to the above, there is an inhaler which allows a user to select a panel member, which a user prefers, and attach it to a main body, for making the inhaler have external appearance that fits preference of the user.

CITATION LIST

Patent Literature

PTL 1: Japanese Patent Application Public Disclosure No. 2012-513750
PTL2: PCT international publication No. WO 2019-084161
PTL3: PCT international publication No. WO 2016-194882

SUMMARY OF INVENTION

Technical Problem

Usually, for allowing a user to set an operation mode of an inhaler, it is necessary to have a construction that requires the user to perform setting via manual inputting manipulation, such as manipulation of a button or the like. In more detail, every time when an inhaler is powered up, a user is required to perform button input and/or command input corresponding to contents of manipulation. For example, a user can switch a light emission mode of an LED (Light Emitting Diode) to the other by pressing predetermined plural buttons a predetermined number of times in a predetermined order. In this regard, user is required to grasp contents of manipulation corresponding to a predetermined setting, by referring to a manual or the like in advance.

On the other hand, since an inhaler heats an inhaled component source for generating inhaled components, safety with respect to generation of heat in the inhaler should be taken into consideration. For example, in the case that an inhaler is downsized to have a body which can be held by a hand of a user, it is necessary to have a measure for preventing a user from a burn due to heat leaked from the inhaler, such as a measure for enhancing thermal insulation by attaching a panel to an outer side of a main body of the inhaler, or the like.

An object of the present disclosure is to provide an inhaler which can improve usability, and improve user's satisfaction and safety with respect to the inhaler. More specifically, one of the objects is to provide an inhaler which can be operated, in accordance with set contents that fit preference of a user, by performing simple and intuitive manipulation, without requiring a user to perform complicated manual input manipulation. Further, one of the objects is to provide an inhaler which takes safety with respect to heat generation into consideration by attaching a panel to a main body thereof, and is able to detect appropriate attaching of the panel. Further, one of the objects is to provide an inhaler in which set contents are changed according to each panel.

Solution to Problem

According to the present disclosure, in a first aspect, an inhaler which comprises a first member and a second member which is constructed to be attachable/detachable to/from the first member is provided. The inhaler comprises: an active functional part constructed in the first member; a passive functional part which is constructed in the second member, and changes its state in response to effect applied by the active functional part; a sensor which is installed in the first member, and detects a state, that is changed, of the passive functional part; and a controller which judges, based on the detected state, attaching of the second member to the first member.

According to the inhaler, a novel method comprising detecting of change in the state of the passive functional in the second member, that is due to effect of the active functional part in the first member, can be used when performing judgment as to whether the second member is being attached to the first member. By the above construction, appropriate attaching of the second member to the first member can be judged, and safety with respect to the inhaler when it is used can be improved.

An inhaler according to a second aspect comprises the inhaler according to the first aspect, wherein: the active functional part comprises a permanent magnet for generating a first magnetic field; the passive functional part comprises a magnetic substance which is magnetized by the first magnetic field for generating a second magnetic field; and the sensor comprises a magnetic sensor for detecting magnetic force that is based on the second magnetic field.

An inhaler according to a third aspect comprises the inhaler according to the first aspect or the second aspect, wherein the magnetic substance in the passive functional part comprises a ferromagnet or a paramagnet.

An inhaler according to a fourth aspect comprises the inhaler according to any one of the first aspect to the third aspect, wherein: the second member is constructed to be held by the first member by plural holding structures; and at least one of the plural holding structures comprises the active functional part and the passive functional part.

An inhaler according to a fifth aspect comprises the inhaler according to the fourth aspect, wherein the at least one of the plural holding structures is constructed to hold the second member attached to the first member by magnetic attraction between the active functional part and the passive functional part.

An inhaler according to a sixth aspect comprises the inhaler according to any one of the first aspect to the fifth aspect, wherein: the active functional part in the first member is positioned to be separated from the sensor; and the separated distance is larger than the distance between the passive functional part and the sensor in the state that the second member is being attached to the first member.

An inhaler according to a seventh aspect comprises the inhaler according to any one of the first aspect to the sixth aspect, wherein the passive functional part in the second member is positioned to be aligned with both the active functional part and the sensor when the second member is attached to the first member.

An inhaler according to an eighth aspect comprises the inhaler according to the seventh aspect, wherein: the passive functional part comprises a base and a leg extending from the leg; and the base is aligned with the active functional part and the leg is aligned with the sensor when the second member is attached to the first member.

An inhaler according to a ninth aspect comprises the inhaler according to the eighth aspect, wherein the sensor detects the state of the leg.

An inhaler according to a tenth aspect comprises the inhaler according to the eighth aspect or the ninth aspect, wherein the separated distance is larger than the distance between the leg and the sensor in the state that the second member is being attached to the first member.

An inhaler according to an eleventh aspect comprises the inhaler according to any one of the first aspect to the tenth aspect, wherein: the first member comprises a manipulation button on a surface to which the second member is attached; and the manipulation button is covered by the second member when the second member is attached to the first member.

An inhaler according to a twelfth aspect comprises the inhaler according to the eleventh aspect, wherein: the inhaler further comprises a heater for heating an inhaled component source for generating inhaled components; and the inhaler is constructed to allow supplying of electric power to the heater when the manipulation button is pressed via the second member.

Further, according to the present disclosure, in a thirteenth aspect, a panel constructed to be attachable/detachable to/from a main-body housing of an inhaler is provided. The panel comprises a magnetic field applicator which comprises a magnetic substance which is magnetized due to effect of a first magnetic field applied by a magnet included in the main-body housing, and applies a second magnetic field; wherein attaching of the panel to the main-body housing is detected as a result that magnetic force, that is based on the second magnetic field applied by the magnetic substance, is detected by a magnetic sensor included in the main-body housing.

According to the panel, a novel method comprising detecting of magnetization of the magnetic substance in the panel, that is due to effect of the magnet in the main-body housing, can be used when performing judgment as to whether the panel is being attached to the main-body housing. By the above construction, appropriate attaching of the panel to the main-body housing can be judged, and safety with respect to an inhaler when it is used can be improved.

A panel according to a fourteenth aspect comprises the panel according to the thirteenth aspect, wherein the panel is held by the main-body housing by magnetic attraction between the magnet in the main-body housing and the magnetized magnetic field applicator.

Further, according to the present disclosure, in a fifteenth aspect, a method for detecting attaching of a panel to a main-body housing of an inhaler is provided. The method includes: detecting magnetic force, that is based on a magnetic field, by a magnetic sensor installed in the main-body housing, wherein a magnetic substance installed in the panel is magnetized due to effect of a magnet included in the main-body housing, and applies the magnetic field to the main-body housing; and judging, in response to detection of the magnetic force based on the magnetic field, a state that the panel is being attached to the main-body housing.

According to the method, a novel method comprising detecting of magnetization of the magnetic substance in the panel, that is due to effect of the magnet in the main-body housing, can be used when performing judgment as to whether the panel is being attached to the main-body housing. By the above construction, appropriate attaching of the panel to the main-body housing can be judged, and safety with respect to an inhaler when it is used can be improved.

A method according to a sixteenth aspect comprises the method according to the fifteenth aspect, wherein the panel is held by the main-body housing by magnetic attraction between the magnet in the main-body housing and the magnetized magnetic substance.

A method according to a seventeenth aspect comprises the method according to the fifteenth aspect or the sixteenth aspect, and further includes inhibiting activation of the inhaler in the case that the attaching is not detected.

A method according to an eighteenth aspect comprises the method according to any one of the fifteenth aspect or the seventeenth aspect, wherein the inhaler comprises a heater for heating an inhaled component source for generating inhaled components and a manipulation button, and the method further includes: accepting pressing of the manipulation button; and allowing supplying of electric power to the heater in response to pressing of the manipulation button, in the case that the value of the detected magnetic force is that within a predetermined range of values.

In addition, according to the present disclosure, in a nineteenth aspect, a program that makes the inhaler perform the method according to any one of the fifteenth aspect to the eighteenth aspect is provided.

Further, according to the present disclosure, in a twentieth aspect, an inhaler, which comprises a first member and a second member which is constructed to be attachable/detachable to/from the first member, is provided. In the inhaler, the first member comprises a heater for heating an inhaled component source for generating inhaled components, and a controller for creating a state wherein heating operation by the heater is allowed, in the case that attaching of the second member to the first member is detected; and the second member insulates heat generated from the heater.

According to the inhaler, appropriate attaching of the panel to the main-body housing can be judged, and, at the same time, the problem relating to heat generation when the inhaler is used can be solved, so that safety with respect to the inhaler when it is used can be improved.

DESCRIPTION OF EMBODIMENTS

In the following description, inhalers according to embodiments of the present disclosure, together with attached figures, will be explained with reference to the figures. In the attached figures, the same or similar reference symbols are assigned to the same or similar components, respectively, and overlapping explanation of the same or similar components may be omitted in the explanation of respective embodiments. Further, a characteristic shown in each embodiment can be applied to the other embodiment as long as they are not contradictory to each other. Further, the figures are drawn in a schematic manner, so that actual sizes, ratios, and so on may not always coincide with those in the figures. Also, in the figures, a figure may include a part wherein relationship in terms of the size, the ratio, or the like is different from that relating to a corresponding part in the other figure.

It should be reminded that, in the explanation of the embodiments of the present disclosure, although inhalers are those which generate materials inhaled by users, and comprise an electronic cigarette and a nebulizer, the inhalers are not limited to those explained above. Specifically, the inhalers may comprise various inhalers for generating aerosol or flavor-added aerosol sucked by users. Further, the generated inhaled components may include gases such as invisible vapor, in addition to aerosol.

1. CONSTRUCTION EXAMPLES OF INHALER

An inhaler 100 (100A, 100B) according to an embodiment will be explained with reference to FIG. 1A and FIG. 1B. In the following description, although it is explained that material generated from the inhaler 100 is aerosol, and an inhaled component source, that is heated, is an aerosol source, they are not limited to those explained herein.

(1) First Construction Example

Figure 1A:
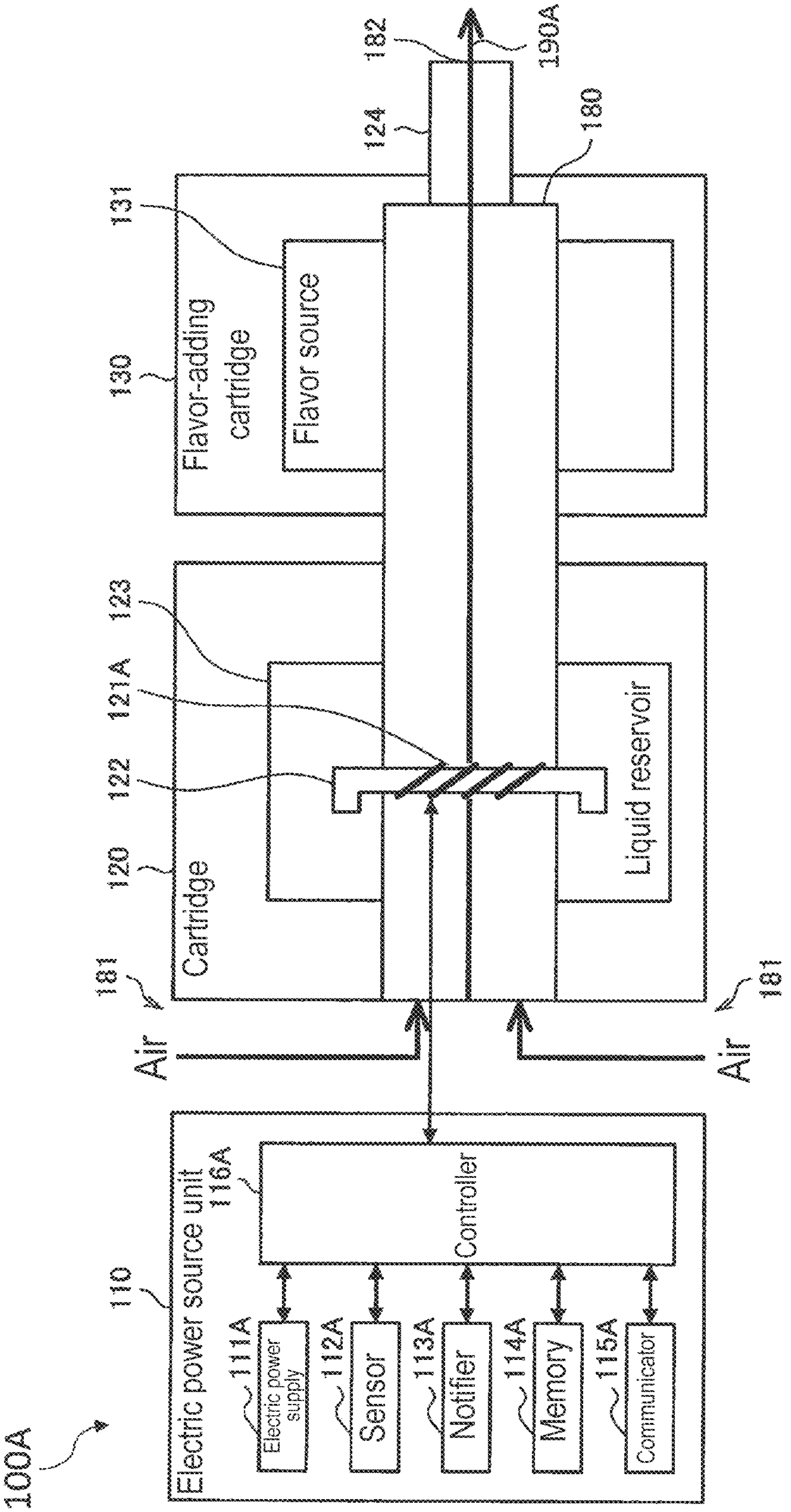
FIG. 1A is a schematic diagram which schematically shows a construction of an example of an inhaler according to an embodiment.

FIG. 1A is a schematic diagram which schematically shows a first construction example of an inhaler. As shown in FIG. 1A, the inhaler 100A according to the present construction example comprises an electric power source unit 110, a cartridge 120, and a flavor-adding cartridge 130. The electric power source unit 110 comprises an electric power supply 111A, a sensor 112A, a notifier 113A, a memory 114A, a communicator 115A, and a controller 116A. The cartridge 120 comprises a heater 121A, a liquid guide 122, and a liquid reservoir 123. The flavor-adding cartridge 130 comprises a flavor source 131 and a mouthpiece 124. An air flow path 180 is formed in the cartridge 120 and the flavor-adding cartridge 130.

The electric power supply 111A stores electric power. Further, the electric power supply 111A supplies, based on control performed by the controller 116A, electric power to respective components of the inhaler 100. The electric power supply 111A may comprise, for example, a rechargeable battery such as a lithium-ion secondary battery or the like.

The sensor 112A obtains various kinds of information relating to the inhaler 100. For example, the sensor 112A comprises a pressure sensor such as a microphone condenser or the like, a flow rate sensor, a temperature sensor, or the like, and obtains values relating to suction performed by a user. In a different example, the sensor 112A comprises an input device, such as a button, a switch, or the like, which receives information inputted from a user.

In an embodiment, the sensor 112A detects attaching of a panel to the main-body housing, and measures data associated with the panel (this will be explained later). For example, the sensor 112A comprises a magnetic sensor (for example, a Hall sensor which uses a Hall element and detects magnetism by using Hall effect). Further, the sensor 112A detects a state that a panel, which comprises a magnetic field applicator (for example, a magnet and/or a magnetic substance) which applies a magnetic field to the magnetic sensor, is positioned close to the sensor 112A, detects magnetic force outputted from the magnetic field applicator, and measures the magnitude thereof. That is, measured data comprises information that is based on the magnitude of the magnetic force detected by the magnetic sensor.

The notifier 113A notifies a user of information. For example, the notifier 113A comprises a light emission device for emitting light (for example, an LED), a display device for displaying an image, a sound outputting device for outputting sound, a vibrating device for outputting vibration, or the like.

The memory 114A stores various kinds of information for operation of the inhaler 100A. For example, the memory 114A comprises a non-volatile storage medium such as a flash memory or the like. Further, the memory 114A also stores programs such as firmware and so on, in addition to computer executable instructions for operation of the inhaler 100A.

In an embodiment, the memory 114A stores plural operation profiles. An operation profile comprises a notification profile relating to a method for controlling the notifier 113A and a heating profile for the heater 121A. In more detail, the notification profile comprises a color of emitted light, a cycle of light emission, and a pattern of light emission of an LED during at least one of a period during that inhaled components are generated and a period during that no inhaled component is generated. On the other hand, the heating profile defines transition of temperature of the heater 121A for heating the heater 121A.

The communicator 115A is a communication interface which allows communication conforming to any wired or wireless communication standard. Regarding the above communication standard, Wi-Fi (a register trade mark), Bluetooth (a register trade mark), or the like, for example, may be adopted in the case of wireless communication. On the other hand, in the case of wired communication, a data communication cable, for example, is connected via an external connection terminal of micro-USB or the like. With the above construction, inputting/outputting of data relating to operation of the inhaler 100A is performed between it and an external device.

The controller 116A functions as an arithmetic processing unit and a controller device, and controls overall operation in the inhaler 100A in accordance with various kinds of programs. The controller is realized by using an electronic circuit such as a CPU (Central Processing Unit), a microprocessor, or the like, for example.

In an embodiment, the controller 116A specifies an operation profile associated with data measured by the sensor 112A. Thereafter, the controller 116A makes the inhaler 100A operate in accordance with the specified operation profile.

The liquid reservoir 123 stores an aerosol source. Aerosol is generated as a result that the aerosol source is atomized. The aerosol source may be liquid such as polyhydric alcohol, such as glycerin, propylene glycol, or the like, or water, or the like, for example. The aerosol source may comprise a flavor component which is or is not originated from tobacco. In the case that the inhaler 100A is an inhaler for medical use, such as a nebulizer or the like, the aerosol source may comprise a medicine.

The liquid guide 122 guides an aerosol source, which is liquid stored in the liquid reservoir 123, from the liquid reservoir 123, and holds it. For example the liquid guide 122 is a wick which is formed by twisting fiber material such as glass fibers or the like, or porous material such as porous ceramics or the like. In such a case, the aerosol source stored in the liquid reservoir 123 is guided by capillary effect occurring in the wick.

The heater 121A heats the aerosol source to atomize the aerosol source to thereby generate aerosol. In the example shown in FIG. 1A, the heater is constructed as a coil, and wound around the liquid guide 122. When heat is generated by the heater 121A, the aerosol source held in the liquid guide 122 is heated and atomized, and aerosol is generated thereby. The heater 121A generates heat when electric power is supplied thereto from the electric power supply 111A. In an example, supplying of electric power may be performed at the time when starting of user's inhalation action, accepting of predetermined user's input manipulation, and/or inputting of predetermined information is detected by the sensor 112A. Further, supplying of electric power may be stopped at the time when termination of user's inhalation action, accepting of predetermined user's input manipulation, and/or inputting of predetermined information is detected by the sensor 112A.

The flavor source 131 is a component for adding flavor components to the aerosol. The flavor source 131 may comprise a flavor component which is or is not originated from tobacco.

The air flow path 180 is a path for air sucked by a user. The air flow path 180 has a tubular structure having two ends, specifically, an air inflow hole 181 which is an inlet for taking air into the air flow path 180, and air outflow hole 182 which is an outlet for releasing air from the air flow path 180. In the middle part of the air flow path 180, the liquid guide 122 is positioned on an upstream side thereof (a side close to the air inflow hole 181), and the flavor source 131 is positioned on a downstream side thereof (a side close to the air outflow hole 182). The air taken from the air inflow hole 181 during suction by a user is mixed with aerosol generated by the heater 121A, passes through the flavor source 131, and is conveyed to the air outflow hole 182, as shown by an arrow 190A. When the fluid mixture comprising aerosol and air passes through the flavor source 131, the flavor components included in the flavor source 131 is added to the aerosol.

The mouthpiece 124 is a member which is held in the user's mouth when suction action is performed. The air outflow hole 182 is positioned in the mouthpiece 124. A user can take the mixed fluid comprising aerosol and air into the user's mouth by holding the mouthpiece 124 in the user's mouth and performing suction action.

In the above description, a construction example of the inhaler 100A has been explained. Although it is needless to state, the construction of the inhaler 100A is not limited to that explained above, and it may have one of various constructions shown below as examples.

In an example, the inhaler 100A may not comprise the flavor-adding cartridge 130. In such a case, the cartridge 120 is provided with the mouthpiece 124.

In a different example, the inhaler 100A may comprise plural kinds of aerosol sources. Plural kinds of aerosol generated from plural kinds of aerosol sources may be mixed in the air flow path 180 and chemical reaction may occur therein, and, as a result, a different kind of aerosol may further be generated.

Further, the measure for atomizing the aerosol source is not limited to heating by the heater 121A. For example, the measure for atomizing the aerosol source may be oscillation atomization or induction heating.

(2) Second Construction Example

Figure 1B:
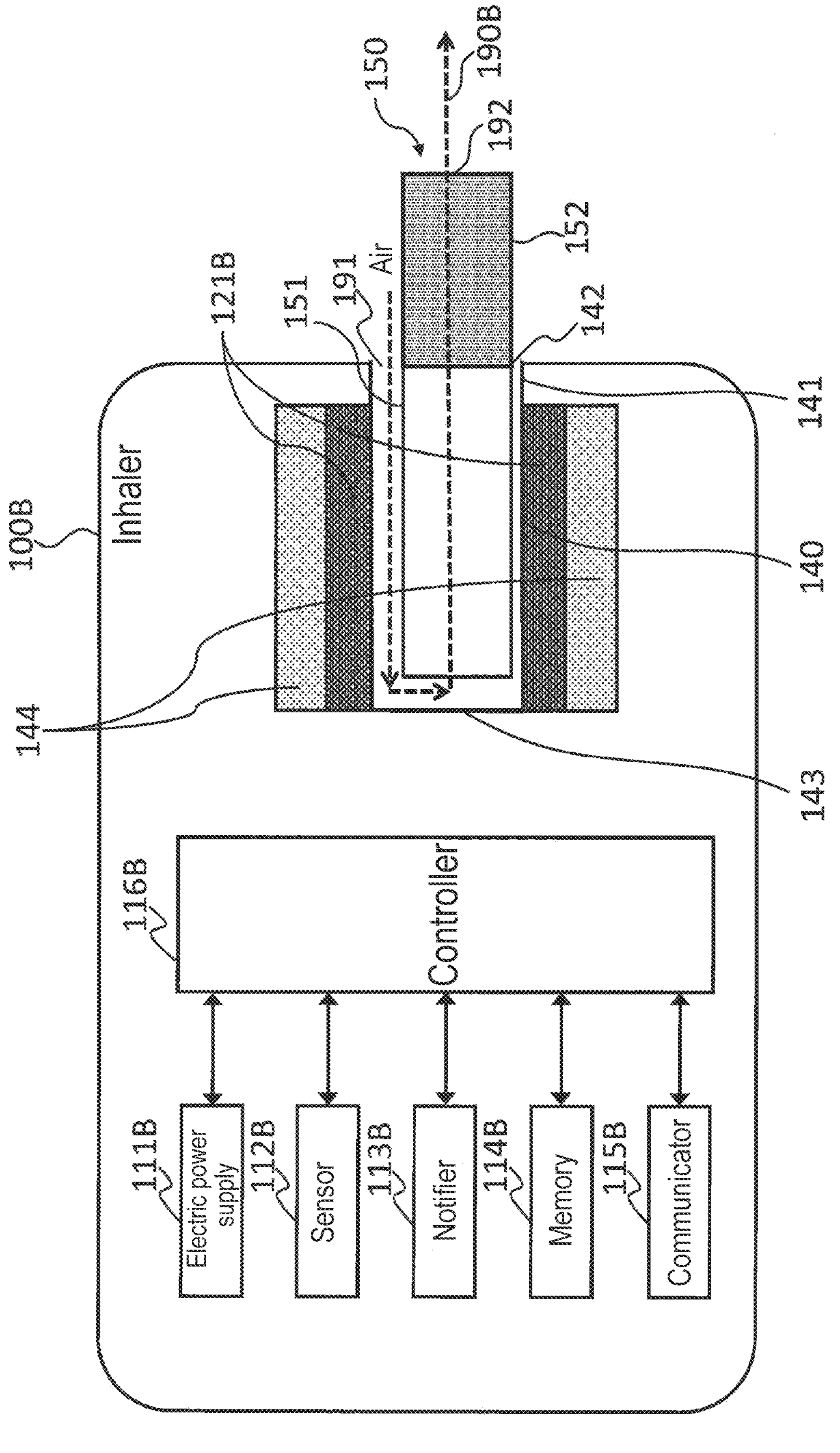
FIG. 1B is a schematic diagram which schematically shows a construction of a different example of an inhaler according to an embodiment.

FIG. 1B is a schematic diagram which schematically shows a second construction example of the inhaler. For example, in an inhaler 100B, a stick-type base material 150 is inserted therein; wherein the stick-type base material 150 comprises a flavor generation base-material such as a filling article comprising a flavor source and an aerosol source which are inhaled component sources, or the like. In this regard, in the present construction example, the aerosol source is not limited to that having a liquid form, and it may be that having a solid form. The inserted stick-type base material 150 is heated from its outer periphery, and thereby generates aerosol including flavor.

As shown in FIG. 1B, the inhaler 100B according to the present construction example comprises an electric power supply 111B, a sensor 112B, a notifier 113B, a memory 114B, a communicator 115B, a controller 116B, a heater 121B, a holding part 140, and a heat insulator 144.

Each of the electric power supply 111B, the sensor 112B, the notifier 113B, the memory 114B, the communicator 115B, and the controller 116B is substantially identical with each of the corresponding components included in the inhaler 100A according to the first construction example.

The holding part 140 comprises an inner space 141, and holds the stick-type base material 150 by housing a part of the stick-type base material 150 in the inner space 141. The holding part 140 comprises an opening 142 which makes the inner space 141 communicate with the outside, and holds the stick-type base material 150 inserted from the opening 142 into the inner space 141. For example, the holding part 140 has a cylindrical shape having the opening 142 and a bottom part 143 which is a bottom plane, and defines a columnar inner space 141. In the present specification, the direction that the stick-type base material 150 is inserted into the columnar inner space 141 is referred to as a longitudinal direction of the inhaler 100B.

The holding part 140 comprises a shutter (which is not shown in the figure) which opens/closes the opening 142. In more detail, the shutter comprises a slide mechanism, and is allowed to be moved between a first position for closing the opening 142 and a second position for opening the opening 142 along a surface of an outer shell. The stick-type base material 150 is inserted into the columnar inner space 141 via the opening 142 in the state that the opening 142 is being opened, and received in the inner space 141. In this regard, the open state and the close state of the opening 142 can be detected by the sensor 112B by installing a sensor(s) (which is/are not shown in the figure) in a position(s) close to the first position and/or the second position. For example, a magnet is installed in the shutter, and open/close states of the opening 142 is detected by a magnetic sensor.

Also, the communicator 115B may activate a communication function by using, as a trigger for activation, a state that the shutter has opened the opening 142, and may start communication with an external terminal by using Bluetooth (a registered trade mark) or the like. Further, it may terminate communication, that is being performed with an external terminal, by using, as a trigger for termination, a state that the shutter has closed the opening 142. Especially, it is preferable to use BLE (Bluetooth Low Energy) connection as the above Bluetooth (a registered trade mark) connection between the communicator 113B and an external terminal.

In the holding part 140, a pressing part and non-pressing part (they are not shown in the figure) are formed on a wall in an inner side of the inner space 141, along the longitudinal direction. When the stick-type base material 150 is received in the inner space 141, the pressing part applies pressing force to the stick-type base material 150 in a direction perpendicular to the longitudinal direction. Thus, the stick-type base material 150 is pressed by the pressing part and deformed thereby, and, in such a state, is held by the holding part 140. As a result, the stick-type base material 150, while it is being pressed, is heated from the outer periphery thereof by the heater 121B.

On the other hand, a vacant space (not shown in the figure) is formed between the non-pressing part and the stick-type base material 150. Thus, communication between the opening 142 and the bottom part 143 is allowed via the vacant space.

The holding part 140 also has a function for defining a path for air that is supplied to the stick-type base material 150. An air inflow hole 191, which is an air inlet to the above path, is the opening 142. More precisely, the air inflow hole 191 is a vacant space between the non-pressing part and the stick-type base material 150. The air taken from the air inflow hole 191 during suction by a user is conveyed, along an arrow represented by a dashed line, to the air outflow hole 192, which is an air outlet of the path, via the stick-type base material 150.

The stick-type base material 150 comprises a base material part 151 and a suction opening part 152. The base material part 151 comprises an aerosol source. In the state that the stick-type base material 150 is being held by the holding part 140, at least a part of the base material part 151 is housed in the inner space 141, and at least a part of the suction opening part 152 protrudes from the opening 142. Thus, when the suction opening part 152, which protrudes from the opening 142, is held in a user's mouth and suction action is performed by the user, air flows into the inner space 141 from the air inflow hole 191, and, along the arrow represented by a dashed line, the air is conveyed to the air outflow hole 192 of the suction opening part 152 via the bottom part 143, and arrives at the inside of the user's mouth, together with aerosol generated from the base material part 151.

The heater 121B comprises a construction similar to that of the heater 121A according to the first construction example. However, in the example shown in FIG. 1B, the heater 121B is constructed to have a film shape, and is arranged to cover the outer periphery of the holding part 140. Thus, when heat is generated by the heater 121B, the base material part 151 of the stick-type base material 150 is heated from the outer periphery thereof, and aerosol is generated accordingly.

The heat insulator 144 prevents heat transfer from the heater 121B to other components. For example, the heat insulator 144 comprises vacuum insulation material, aerogel insulation material, or the like.

In the above description, a construction example of the inhaler 100B has been explained. Although it is needless to state, the construction of the inhaler 100B is not limited to that explained above, and it may have one of various constructions shown below as examples.

For example, the heater 121B may be constructed to have a blade shape, and arranged to protrude from the bottom part 143 to the inner space 141 of the holding part 140. In such a case, the blade-shape heater 121B is inserted into the base material part 151 of the stick-type base material 150, and the base material part 151 of the stick-type base material 150 is heated from the inside thereof. In a different example, the heater 121B may be arranged to cover the bottom part 143 of the holding part 140. Further, the heater 121B may be constructed as that comprising a combination of two or more of a first heater covering the outer periphery of the holding part 140, a second heater having a blade shape, and a third heater covering the bottom part 143 of the holding part 140.

Further, the measure for atomizing the aerosol source is not limited to heating by the heater 121B. For example, the measure for atomizing the aerosol source may be induction heating.

Further, the inhaler 100B may comprise the heater 121A, the liquid guide 122, the liquid reservoir 123, and the air flow path 180 according to the first construction example, and the air outflow hole 182 of the air flow path 180 may double as an air inflow hole to the inner space 141. In such a case, the fluid mixture comprising air and aerosol generated by the heater 121A flows into the inner space 141, is further mixed with aerosol generated by the heater 121B, and arrives at the inside of a user's mouth.

2. CONSTRUCTION EXAMPLE OF EXTERIOR OF INHALER

The exterior of the inhaler 100 according to an embodiment will be explained. In the following description, although explanation with respect to the inhaler 100B according to the second construction example shown in FIG. 1B will be provided, it is not limited thereto, and it is similarly applicable to the inhaler 100A in FIG. 1A.

Figure 2:
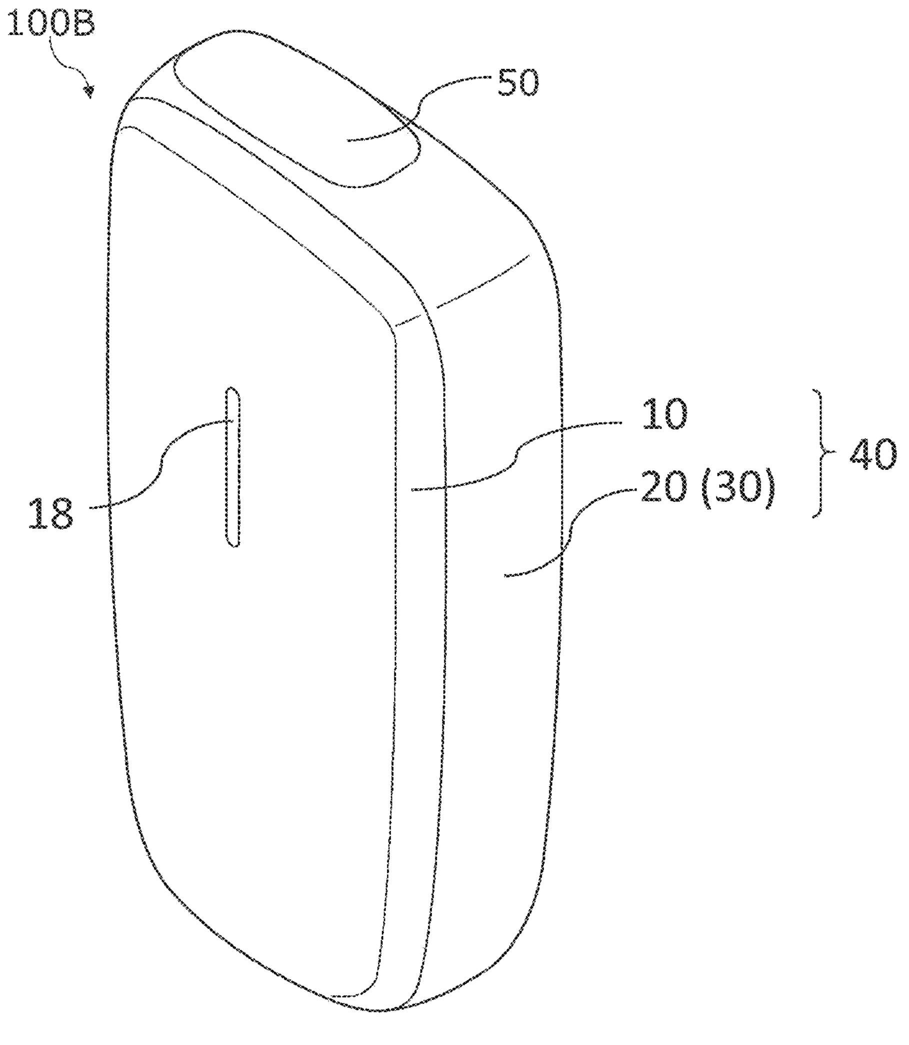
FIG. 2 is a general perspective view of the inhaler in FIG. 1B.

FIG. 2 is a general perspective view of the inhaler 100B. The inhaler 100B comprises a panel 10, a main-body housing 20 to/from which the panel 10 is attachable/detachable, and a shutter 50. The panel 10 and the main-body housing 20 comprise members which are different from each other, respectively. The panel 10 comprises, on its surface, an indicator 18 which comprises transparent material. In this regard, it is preferable that respective types of panels 10 be constructed in such a manner that they have outer surfaces having different designs comprising different patterns and colors, and are constructed by using different materials, and so on, respectively. For example, a panel of the type "Panel a for male" is a panel designed to have a camouflage pattern, a panel of the type "Panel b for female" is a panel designed to have pink-painted part, and so on. A user may appropriately select a type of a panel that fits preference of the user. The main-body housing 20 houses the main body 30 of the inhaler 100B. The respective components of the inhaler 100B shown in FIG. 1B are housed in the main body 30.

The outermost housing 40 of the inhaler 100B is formed by attaching the panel 10 to the main-body housing 20. By attaching a panel 10 which has a design that fits user's preference, fashionability with respect to the inhaler 100B can be improved. Further, by having the panel 10, the inhaler 100B can buffer heat emitted to the outside when the main body 30 is heated. That is, the panel 10 functions to insulate heat generated from the heater 121B. Further, the panel 10 is constructed to have a surface which is substantially a curved surface. Thus, when the panel 10 is attached to the main-body housing 20, the panel 10 and the surface of the main-body housing 20 together define an inner space.

It is preferable that the housing 40 be constructed to have a size that fits a hand of a user. A user touches the surface of the panel 10 by user's fingers and holds the inhaler 100B by a hand. Further, the panel 10 is deformed to be dented toward the main-body housing 20, as a result that the surface of the panel 10 is pushed by tips of fingers of a user. As a result of such deformation of the panel 10, a protrusion formed on the panel 10 is brought into contact with a manipulation button formed on a surface of the main-body housing 20, and the manipulation button is pressed accordingly (this will be explained later).

For deforming the panel 10, a user is required to push the surface by using plural fingers at the same time, for example. In the above case, more pressing force is required, when compared, for example, with that of the case wherein a single button constructed to protrude from the surface of the housing is pushed by a single finger of a user. That is, the inhaler 100B according to the embodiment is advantageous in the point that unintentional erroneous manipulation by a user, such as erroneous pressing of the manipulation button in a bag, and so on, can be prevented. Further, since it is not easy to deeply press the surface of the panel 10 by applying pressing force exerted by a child who is not appropriate as a user of the inhaler 100B, it is advantageous in terms of prevention of mischief (child-resistant)

In FIG. 2, a state that the opening 142 is being closed by the shutter 50 is shown. The opening 142 is opened by touching the shutter 50 by a user's finger and sliding it along a side surface. After opening the opening 142, a user is allowed to insert the stick-type base material 150. After inserting the stick-type base material 150, a user can power up the inhaler 100B, by pressing the manipulation button by pressing the surface of the panel 10.

3. CONSTRUCTION EXAMPLES OF RESPECTIVE EXTERIORS OF PANELS AND MAIN-BODY HOUSINGS

The exterior of a pair of a panel 10 and a main-body housing 20, which are components of the inhaler 100 (100A, 100B) according to an embodiment will be explained with reference to FIG. 3A to FIG. 4B. In the following description, although an example relating to the inhaler 100B shown in FIG. 1B will be shown, it is not limited thereto, and it is similarly applicable to the inhaler 100A in FIG. 1A.

(1) First Construction Example of Panel and Main-body Housing

Figure 3A:
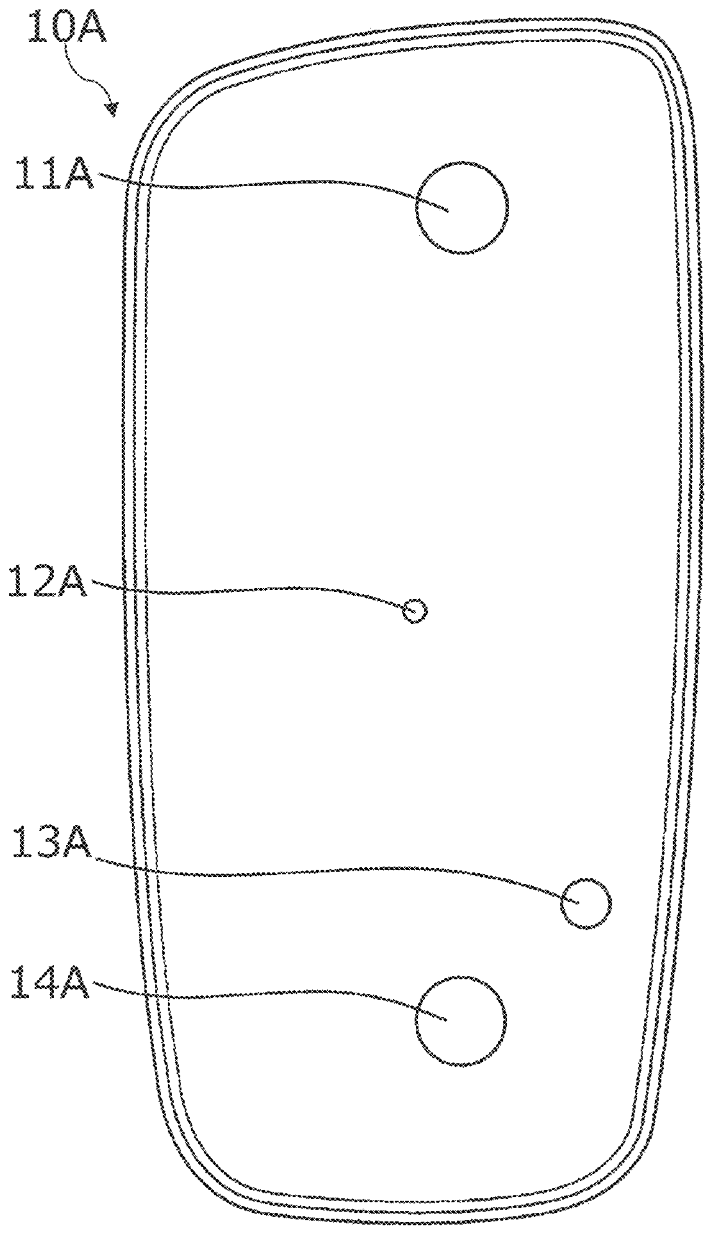
FIG. 3A is a schematic external view of an example of a panel which is a component of the inhaler in FIG. 1B.
Figure 3B:
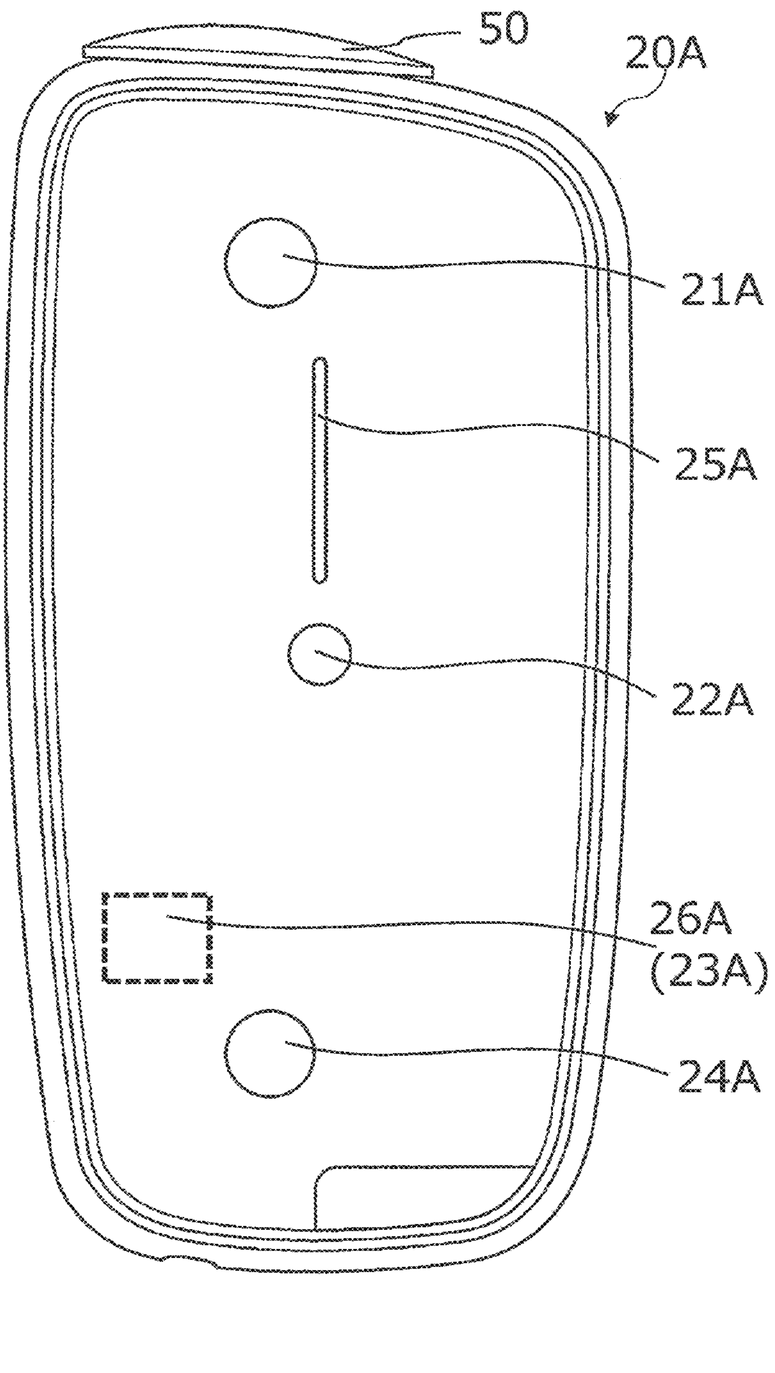
FIG. 3B is a schematic external view of an example of a main-body housing which is a component of the inhaler in FIG. 1B.

FIG. 3A and FIG. 3B show a pair of a panel 10A and a main-body housing 20A according to a first construction example of the inhaler 100B. FIG. 3A is an external view of an inner-side surface of the panel 10A, and FIG. 3B is an external view of an outer-side surface of the main-body housing 20A. In the state that the panel 10A is attached to the main-body housing 20A, the inner-side surface of the panel 10A and the outer-side surface of the main-body housing 20A face each other.

As shown in FIG. 3A, a magnet 11A, a projection 12A, a magnet 13A, and a magnet 14A are arranged in the longitudinal direction on the inner-side surface of the panel 10A. When the panel 10A is attached to the main-body housing 20A, the magnet 11A and the magnet 14A attract the main-body housing 20A by their magnetic force (magnetic attraction). As a result, the panel 10A is held by the main-body housing 20A. The projection 12A pushes a manipulation button 22A installed on the surface of the main-body housing 20A. The magnet 13A is constructed as a magnetic field applicator relating to the sensor 112B in the main body 30. That is, it is constructed to detect the panel 10A, by making a magnetic sensor 23A in the main-body housing 20A detect magnetic force from a magnetic field applied from the magnet 13A.

As shown in FIG. 3B, on the outer-side surface of the main-body housing 20A, a magnet 21A, an indicator window 25A, a manipulation button 22A, and a magnet 24A are arranged in the longitudinal direction from the side of the shutter 50. Further, on the inner-side surface of the main-body housing 20A (more precisely, on a circuit board which is arranged in such a manner that the distance between it and the inner-side surface is substantially zero), a magnetic sensor 23A is arranged in a position that is between the manipulation button 22A and a magnet 24A and in the longitudinal direction. A magnetic force detecting area (the area in a dashed line) 26A is formed in the outer-side surface of the main-body housing 20A by the magnetic sensor 23A. The magnet 21A, the manipulation button 22A, the magnetic sensor 23A, and the magnet 24A in the main-body housing 20A correspond to the magnet 11A, the projection 12A, the magnet 13A, and the magnet 14A in the panel 10A, respectively. That is, they are aligned with one another and face one another, respectively, when the panel 10A is attached to the main-body housing 20A.

The magnet 21A and the magnet 24A in the main-body housing 20A attract, by their magnetic force (magnetic attraction), the magnet 11A and the magnet 14A in the panel 10A, respectively. That is, the magnet 11A and the magnet 21A attract each other, and the magnet 14A and the magnet 24A attract each other, so that the panel 10A is held by the main-body housing 20A in an attachable manner. In this regard, it is preferable that each of the magnet 11A and the magnet 14A in the panel 10A and the magnet 21A and the magnet 24A in the main-body housing 20A be constructed by a permanent magnet.

The manipulation button 22A is installed on the surface to which the panel 10 A is attached. That is, the manipulation button 22A is covered by the panel 10A, when the panel 10A is attached to the main-body housing 20A. It is pushed by the projection 12A in the panel 10A. By the above construction, turning on of the electric power supply and turning off of the electric power supply in the inhaler 100B can be switched between them, for example.

The magnetic sensor 23A detects magnetic force that is based on a magnetic field applied from the magnet 13A in the panel 10A. For example, it is preferable that the magnetic sensor 23A be a Hall sensor which comprises a Hall element. By the above construction, attaching of the panel 10A to the main-body housing 20A can be detected. The indicator window 25A is an opening which is aligned with one or more LEDs arranged in the main body 30, and allows the light from the LED(s) to be transmitted toward the indicator 18 in the panel 10A. By the above construction, a user can visually recognize the light, from the outer-side surface of the panel 10A.

In this regard, the LED is constructed as the notifier 113B, and performs predetermined notification action in accordance with a specified operation profile. For example, the LED notifies information of operation of the inhaler 100B by functioning in a predetermined light emission mode. Specifically, the LED performs light emission for presenting, to a user, a state as to whether the inhaler 100B is being powered up, a state of progress of preheating, a suction condition (the remaining time during that suction is allowable, and so on), and an operation mode that the inhaler 100B is presently in (for example, a suction mode and/or a communication mode, and so on).

The magnetic sensor 23A in the main-body housing 20A is arranged in such a manner that it faces the magnet 13A in the panel 10A via the inner-side surface of the main-body housing 20A, in the state that the panel 10A is being attached to the main-body housing 20A. That is, when the panel 10A is attached to the main-body housing 20A, the distance between the magnetic sensor 23A in the main-body housing 20A and the magnet 13A in the panel 10A becomes the minimum.

Further, the magnetic sensor 23A in the main-body housing 20A is constructed in such a manner that it does not detect a magnetic field generated by each of the two magnets, specifically, the magnet 21A and the magnet 24A, in the main-body housing 20A. Specifically, it is preferable that the magnetic sensor 23A be arranged, on the inner-side surface of the main-body housing 20A, in a position that is distant from the two magnets, specifically, the magnet 21A and the magnet 24A, on the outer-side surface of the main-body housing 20A. By the above construction, effect of the magnetic fields generated from the two magnets, specifically, the magnet 21A and the magnet 24A, can be reduced to approximately zero, in the magnetic sensor 23A.

Further, it is preferable to adopt the construction such that the distance between the magnetic sensor 23A and the magnet 24A (or the magnet 21A) in the main-body housing 20A is set to be larger than the distance between the magnet 13A and the magnetic sensor 23A in the state that the panel 10A is being attached to the main-body housing 20A. By the above construction, effect of the magnetic field applied from the magnet 13A only can be considered appropriately, without considering effect of the magnetic field of the magnet 24A, in the magnetic sensor 23A when detecting attaching of the panel 10A to the main-body housing 20A.

In an embodiment, the respective panels 10A are constructed in such a manner that the respective pieces of data measured by the magnetic sensor 23A when the respective panels 10A are attached to the main-body housing 20A are different from one another according to respective types of the panels 10A. In more detail, the respective panels 10A are constructed in such a manner that the respective quantities of the magnetic force, that relate to the magnets 13A in the magnetic field applicators in the panels 10A and are detected by the magnetic sensor 23A in the main-body housing 20A, are different from one another according to the respective panel types.

For example, it is preferable that the panels 10A be constructed in such a manner that the distances between the magnets 13A of the magnetic field applicators and the facing magnetic sensor 23A, in the state that each of the panels 10A is attached to the main-body housing 20A, are different from one another according to the types of the panels 10A. That is, for making the heights of the inner-side surfaces of the panels 10A different from one another according to the types, it is preferable to adjust the shapes of curved surfaces according to the panel types, respectively. In this regard, in general, a person skilled in the art understands that the magnitude of the magnetic power changes according to the distance from a magnet (specifically, it is inversely proportional to the square of the distance). Thus, a magnet which is the same as the magnet 13A can be used in any type of the panel 10A, so that it is advantageous in terms of manufacture.

In a different example, the magnets 13A may be arranged in positions along the inner-side surfaces of the facing panels 10A, respectively, in such a manner that the positions are shifted from one another according to the panel types. For example, in the case of the following panel types, "Panel a for male" and "Panel b for female," it is preferable that the magnets 13A be arranged in such a manner that they are arranged in different positions by shifting the positions from each other on the inner-side surface of the panels 10A. By the above construction, it becomes possible to make the respective distances between the magnets 13A and the magnetic sensor 23A different from one another according to respective panel types. That is, it becomes possible to make the magnitude of the magnetic power, that is to be detected by the magnetic sensor 23A, different from the other, according to respective panel types.

In a further different example, it is preferable that the panels 10A be constructed in such a manner that types of the magnets 13A in the magnet field applicators are different from one another according to the panel types, respectively. It is preferable that the magnet 13A comprise a permanent magnet. In more detail, a ferrite magnet, an alnico magnet, a cobalt magnet, a neodymium magnet, and so on may be adopted according to the panel types. It is preferable to adopt a construct such that the types of magnets 13A are different from one another according to the panel types, for example, by adopting a ferrite magnet as the magnet 13A when the panel type is "Panel a for male" and adopting an alnico magnet as the magnet 13A when the panel type is "Panel b for female." By the above construction, it becomes possible to make the magnitude of the magnetic power, that is to be detected by the magnetic sensor 23A, different from the other, according to respective panel types.

In addition, regarding the types of the magnets 13A corresponding to the panel types, it is preferable to adopt appropriate types based on specifications of the main bodies 30 and/or the panels 10A of the inhalers 100B. For example, it is preferable to adopt a ferrite magnet which outputs weak magnetic force, in the case that magnetic force from a magnet exerts a bad influence on the behavior of the main body 30 of the inhaler 100B. Further, it is preferable to adopt an alnico magnet which has a characteristic that high temperature stability is high, in the case that the panel 10A is constructed by using a material having a characteristic that the temperature thereof rises easily. By the above construction, magnets having appropriate characteristics corresponding to the specifications of the main bodies 30 of the inhalers 100B are installed to the panels 10A, respectively, stability of operation of respective inhalers 100B can be improved.

(2) Second Construction Example of Panel and Main-body Housing

Figure 4A:
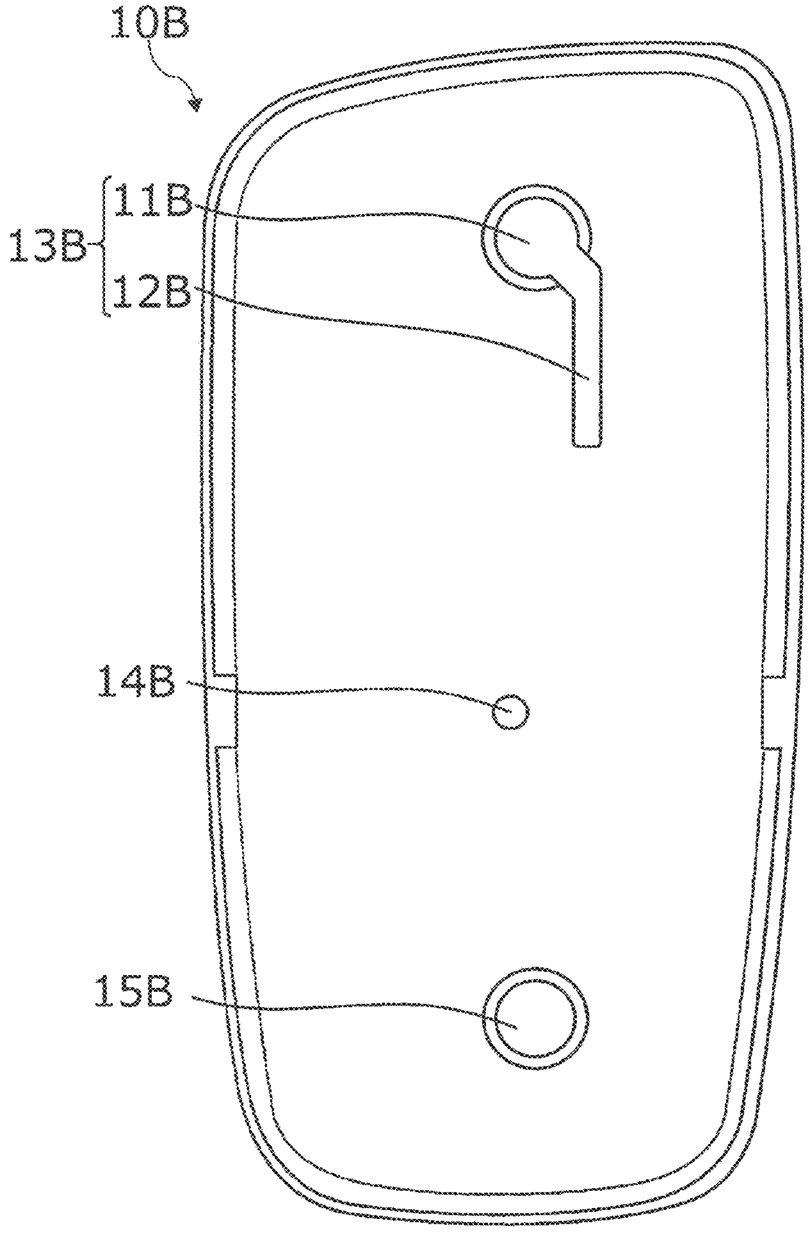
FIG. 4A is a schematic external view of a different example of a panel which is a component of the inhaler in FIG. 1B.
Figure 4B:
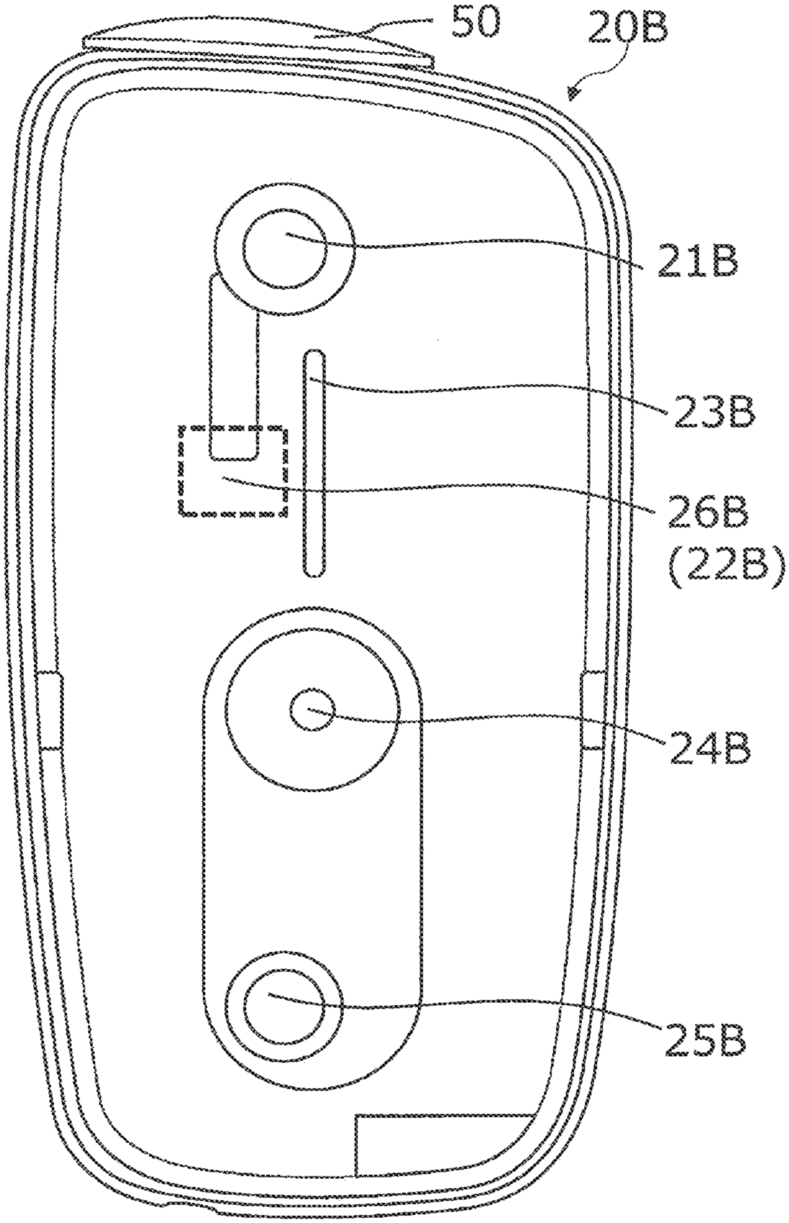
FIG. 4B is a schematic external view of a different example of a main-body housing which is a component of the inhaler in FIG. 1B.

FIG. 4A and FIG. 4B show a pair of a panel 10B and a main-body housing 20B according to a second construction example of the inhaler 100B. FIG. 4A is an external view of an inner-side surface of the panel 10B, and FIG. 4B is an external view of an outer-side surface of the main-body housing 20B. In the state that the panel 10B is attached to the main-body housing 20B, the inner-side surface of the panel 10B and the outer-side surface of the main-body housing 20B face each other.

As shown in FIG. 4A, a magnetic substance 13B, a projection 14B, and a magnet 15B are arranged in the longitudinal direction on the inner-side surface of the panel 10B. Further, the magnetic substance 13B comprises a circular base 11B and a leg 12B which extends linearly from the base 11B in an approximately longitudinal direction.

The magnetic substance 13B is constructed by using material which becomes magnetized due to effect of a magnetic field when the magnetic field is applied thereto from the outside, and applies a magnetic field. The magnetic substance 13B is constructed as a magnetic field applicator which relates to a sensor 112B in the main body 30. It is preferable that the magnetic substance 13B comprise a metal.

In more detail, it is preferable that the magnetic substance 13B comprise a paramagnet or a ferromagnet which is a non-permanent magnet. In this regard, ferromagnetism is a property wherein, when a magnetic field is applied from the outside, a material becomes magnetized strongly in a direction that is the same as the direction of the magnetic field, and strong magnetism remains therein even if the magnetic field applied from the outside is reduced to zero. Examples of ferromagnetic materials are iron, cobalt, and nickel. Further, paramagnetism is a property wherein, when a magnetic field is applied from the outside, a material becomes magnetized weakly in a direction that is the same as the direction of the magnetic field, and loses obtained magnetism if the magnetic field applied from the outside is reduced to zero. An example of a paramagnetic material is aluminum.

The magnetic substance 13B is constructed as a passive functional part with respect to which the state thereof changes (i.e., it is magnetized) in response to effect of a magnetic field applied from the outside. In addition, the magnetic substance 13B is constructed as a magnetic field applicator for applying a magnetic field to the main-body housing 20B.

Specifically, when the panel 10B is attached to the main-body housing 20B, the magnetic substance 13B functions as a passive functional part which receives an effect from the magnet 21B in the main-body housing 20B. As a result, the magnetic substance 13B becomes magnetized, and, then, it functions as a magnetic field applicator for the magnet 21B and the magnetic sensor 22B in the main-body housing 20B.

In more detail, by the magnetic force that is based on the magnetic field generated in the magnetic substance 13B (especially, the base 11B) and applied therefrom, the panel 10B can be attracted to the main-body housing 20B and held thereby. Further, in relation to the magnetic field generated in the magnetic substance 13B (especially, the leg 12B) and applied therefrom, it is possible to make the magnetic sensor 22B in the main-body housing 20B detect the state of the leg 12B (i.e., the magnetic force based on the magnetic field from the leg 12B). By the above construction, it becomes possible to make the main-body housing 20B detect attaching of the panel 10B thereto.

As shown in FIG. 4B, on the outer-side surface of the main-body housing 20B, a magnet 21B, an indicator window 23B, a manipulation button 24B, and a magnet 25B are arranged in the longitudinal direction from the side of the shutter 50. Further, on the inner-side surface of the main-body housing 20B (more precisely, on a circuit board which is arranged in such a manner that the distance between it and the inner-side surface is substantially zero), a magnetic sensor 22B is arranged, in the longitudinal direction, in a position that is between the manipulation button 24B and a magnet 21B and beside the indicator window 23B. A magnetic force detecting area (the area in a dashed line) 26B is formed in the outer-side surface of the main-body housing 20B by the magnetic sensor 22B.

The magnet 21B, the magnetic sensor 22B, the manipulation button 24B, and magnet 25B in the main-body housing 20B correspond to the base 11B of the magnetic substance 13B, the leg 12B of the magnetic substance 13B, the projection 14B, and the magnet 15B in the panel 10B, respectively. That is, they are aligned with one another and face one another, respectively, when the panel 10A is attached to the main-body housing 20A.

Specifically, the components are positioned in such a manner that, when the panel 10B is attached to the main-body housing 20B, the magnetic substance 13B in the panel 10B is aligned with both the magnet 21B and the magnetic sensor 22B in the main-body housing 20B. In more detail, they are arranged in such a manner that the base 11B of the magnetic substance 13B in the panel 10B is to be aligned with the magnet 21B in the main-body housing 20B, and, at the same time, the leg 12B of the magnetic substance 13B in the panel 10B is to be aligned with the magnetic sensor 22B in the main-body housing 20B. Especially, the magnetic sensor 22B faces, via the inner-side surface of the main-body housing 20B, the leg 12B of the magnetic substance 13B when the panel 10B is attached to the main-body housing 20B, and, as a result, the distance between the magnetic sensor 22B and the leg 12B of the magnetic substance 13B becomes the minimum.

The magnet 21B in the main-body housing 20B is constructed as an active functional part which generates a magnetic field. Thus, it functions to magnetize the magnetic substance 13B in the panel 10B by the magnetic force based on the magnetic field, and attracts the base 11B of the magnetic substance. That is, the panel 10B is held in an attachable manner by the main-body housing 20B, as a result that the base 11B of the magnetic substance 13B and magnet 21B pull each other by magnetic attraction.

Further, the magnetic sensor 22B detects magnetic force of the leg 12B of the magnetized magnetic substance 13B in the panel 10B. For example, similar to the magnetic sensor 23A, it is preferable that the magnetic sensor 22B be a Hall sensor which comprises a Hall element. By the above construction, attaching of the panel 10B to the main-body housing 20B can be detected.

It is preferable to construct the magnetic sensor 22B in the main-body housing 20B in such a manner that it does not detect a magnetic field generated by each of the two magnets, specifically, the magnet 21B and the magnet 25B, in the main-body housing 20B. Specifically, it is preferable that the magnetic sensor 22B be arranged, on the inner-side surface of the main-body housing 20B, in a position that is distant from the two magnets, specifically, the magnet 21B and the magnet 25B, on the outer-side surface of the main-body housing 20B. By the above construction, effect of the magnetic fields generated from the two magnets, specifically, the magnet 21B and the magnet 25B, can be reduced to approximately zero, in the magnetic sensor 22B.

In an embodiment, it is preferable to adopt a construct such that the distance between the magnetic sensor 22B and the magnet 21B (or the magnet 25B) in the main-body housing 20B is set to be larger than the distance between the magnetic substance 13B and the magnetic sensor 22B in the state that the panel 10B is being attached to the main-body housing 20B. In more detail, it is preferable to adopt a construct such that the distance between the magnetic sensor 22B and the magnet 21B in the main-body housing 20B is set to be larger than the distance between the leg 12B of the magnetic substance 13B in the panel 10B and the magnetic sensor 22B in the main-body housing 20B. By the above construction, the magnetic field applied from the leg 12B of the magnetic substance 13B only can be considered appropriately, without considering effect of the magnetic fields of the two magnets, i.e., the magnet 21B and the magnet 25B, in the magnetic sensor 22B when detecting attaching of the panel 10B to the main-body housing 20B.

It should be reminded that the constructions of the projection 14B and the magnet 15B in the panel 10B and the indicator window 23B, the manipulation button 24B, and the magnet 25B in the main-body housing 20B are similar to the constructions of the projection 12A and the magnet 14A in the panel 10A and the indicator window 25A, the manipulation button 22A, and the magnet 24A in the main-body housing 20A, respectively. Especially, the panel 10B is held in an attachable manner by the main-body housing 20B, as a result that the magnet 15B in the panel 10B and the magnet 25B in the main-body housing 20B pull each other by magnetic attraction.

In an embodiment, the respective panels 10B are constructed in such a manner that the pieces of data measured by the magnetic sensor 22B when the respective panels 10B are attached to the main-body housing 20B are set to be different from one another according to respective types of the respective panels 10B. In more detail, the respective panels 10B are constructed in such a manner that the pieces of data that relate to the magnetized magnetic substances 13B in the panels 10B, respectively, and are detected by the magnetic sensor 22B in the main-body housing 20B (that is, the quantities of the magnetic force detected by the magnetic sensor 22B) are different from one another according to the respective panel types.

For example, it is preferable to set the types of magnetic substances 13B to be different from one another according to the panel types, for example, by adopting iron which is a ferromagnetic material as the magnetic substance 13B when the panel type is "Panel a for male" and adopting aluminum which is a paramagnetic material when the panel type is "Panel b for female," By adopting the construction such that the respective types of metals adopted in the respective magnetic substances 13B are different from one another according to the respective panel types as explained above, it becomes possible to make the magnitude of the magnetic power, that is to be detected by the magnetic sensor 22B, different from the other, according to respective panel types.

Further, it is preferable that the panels 10B be constructed in such a manner that the distances between the legs 12B of the magnetic substances 13B and the facing magnetic sensor 22B, in the state that each of the panels 10B is attached to the main-body housing 20B, are different from one another according to the types of the panels 10B. That is, for making the heights of the inner-side surfaces of the panels 10B different from one another according to the types, it is preferable to adjust the shapes of curved surfaces according to the panel types, respectively. In this regard, in general, a person skilled in the art understands that the magnitude of the magnetic power changes according to the distance from a magnet (specifically, it is inversely proportional to the square of the distance). Thus, a magnetic substance which is the same as the magnetic substance 13B can be used in any type of the panel 10B, so that it is advantageous in terms of manufacture.

In a different example, the magnetic substances 13B may be arranged in positions along the inner-side surfaces of the facing panels 10B, respectively, in such a manner that the positions are shifted from one another according to the panel types. For example, in the case of the following panel types, "Panel a for male" and "Panel b for female," it is preferable that the magnetic substances 13B be arranged in such a manner that they are arranged in different positions by shifting the positions from each other on the inner-side surface of the panels 10B. Especially, it is preferable to arrange the legs 12B of the magnetic substances 13B in such a manner that the positions thereof are different from each other. By the above construction, it becomes possible to make the distances between the respective magnetic substances 13B and the magnetic sensor 22B different from one another according to respective panel types. That is, it becomes possible to make the magnitude of the magnetic power, that is to be detected by the magnetic sensor 22B, different from the other, according to respective panel types.

4. OPERATION EXAMPLE OF INHALER

Figure 5A:
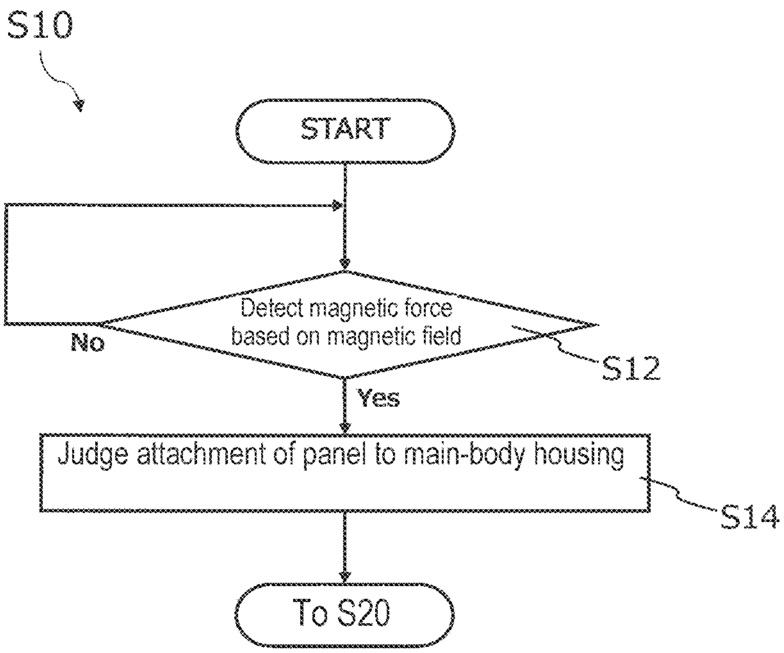
FIG. 5A is a schematic flow chart of operation of an inhaler according to an embodiment.
Figure 5B:
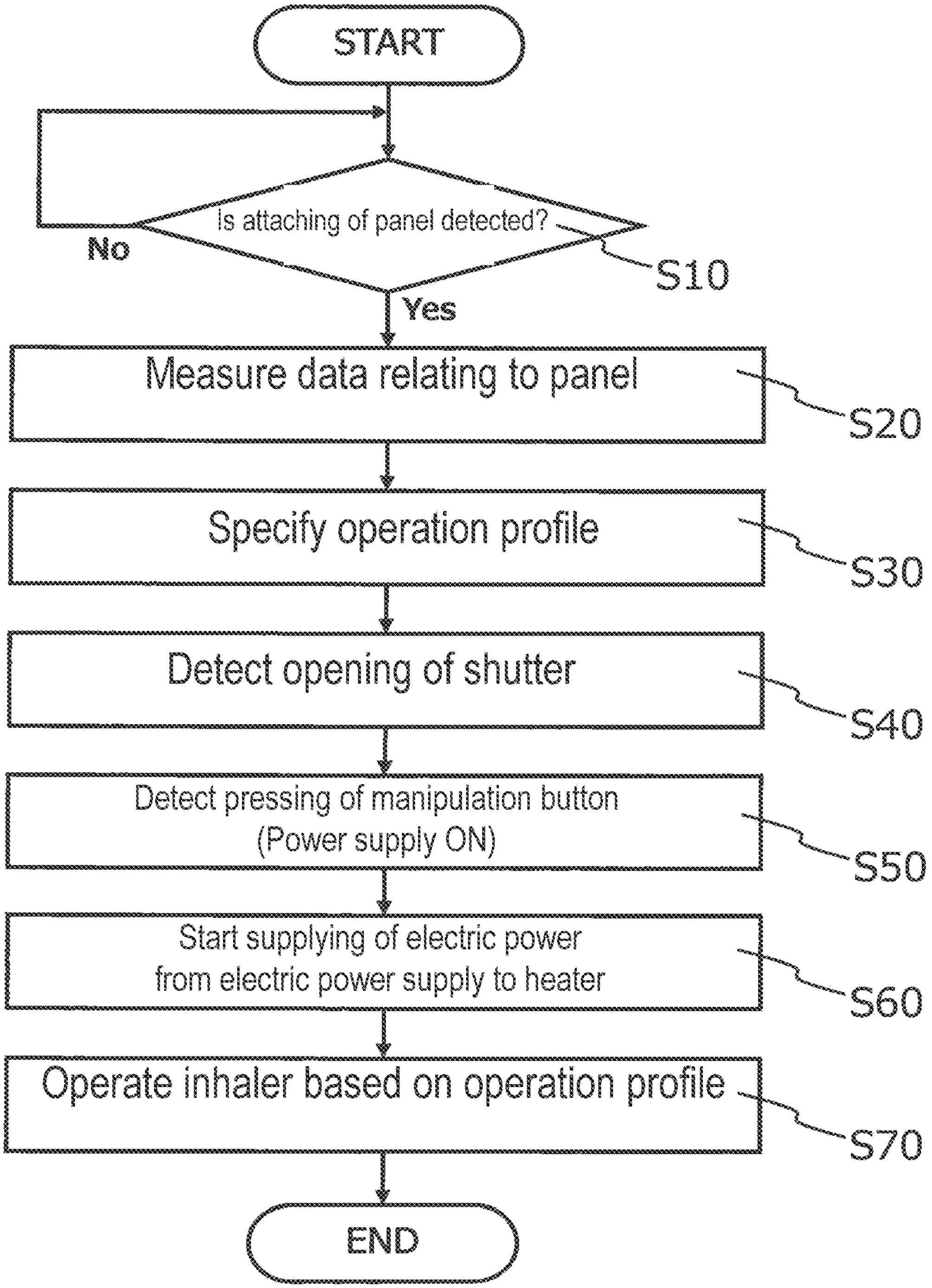
FIG. 5B is a schematic flow chart of operation of an inhaler according to an embodiment.

A schematic operation example of the inhaler 100 according to an embodiment will be explained with reference to FIG. 5A and FIG. 5B. FIG. 5A is a flow chart which relates to operation of the inhaler 100, especially, it relates to operation for judging whether the panel 10 has been attached to the housing 20. Further, FIG. 5B is a schematic flow chart relating to overall operation of the inhaler 100.

In the following description, although the operation that relates to the inhaler 100B shown in FIGS. 1B and 1*s* performed by the controller 116B will be shown, the operation of the inhaler 100 is not limited to it. For example, it is similarly applicable to the inhaler 100A shown in FIG. 1A. Further, although the inhaler 100B, which adopts the panel 10B and the main-body housing 20B shown in FIG. 4A and FIG. 4B will be shown as an example, the operation of the inhaler 10 is not limited to it. For example, it is similarly applicable to the panel 10A and the main-body housing 20A in the inhaler 100B shown in FIG. 3A and FIG. 3B. Further, respective steps shown in FIG. 5A and FIG. 5B are mere examples, and other optional steps may be include therein, and the order of operation of the respective steps is not limited to that explained, as long as a note relating thereto is not specially written.

First, in relation to action of a user to attach the panel 10B to the main-body housing 20B, the controller 116B judges whether the sensor 112B has detected attaching (S10). As explained above, in the case that attaching of the panel 10B to the main-body housing 20B is being performed, the magnetic substance 13B installed in the panel 10B is affected by the magnet 21B installed in the main-body housing 20B, and a state that a magnetic field is being applied to the main-body housing 20B is produced.

Specifically, the controller 116B makes the magnetic sensor 22B installed in the main-body housing 20B detect magnetic force that is based on the applied magnetic field (S12). In the case that the panel 10B has been attached to the main-body housing 20B, magnetic force that is based on the magnetic field applied to the main-body housing 20B is detected (Yes). On the other hand, attaching has not been performed, such a magnetic field is not detected (No). That is, in the case that magnetic force has been detected, the controller 116B judges that the panel 10B is being attached to the main-body housing 20B (S14).

In the case that the sensor 112B has detected attaching of the panel 10B (S10: Yes), the inhaler 100B changes its state to a state wherein manipulation by a user for powering up is allowable. Specifically, the inhaler 100B changes its state to a state wherein manipulation for pressing the manipulation button 24B is acceptable. That is, as a result of S10, the inhaler 100B enters a state wherein it allows supplying of electric power from the electric power supply 111B to the heater 121B, and becomes a state wherein it allows heating operation by the heater 121B.

In this regard, in the state wherein heating operation by the heater 121B is allowable, the controller 116B can allow supplying of electric power from the electric power supply 111B to the heater 121B, after receiving a request for supplying of electric power. Such a request includes, for example, a request generated by performing, by a user, manipulation for pressing the manipulation button 24B, a request generated in response to a state that the opening 142 is being opened as a result of manipulation of the shutter 50 performed by a user, and a request received from a external device via the communicator 115B.

Following the above process, the controller 116B makes the sensor 112B measure data associated with the panel 10B attached to the main-body housing 20B (S20). Specifically, the magnitude of the magnetic force, that is detected in S10, may be measured.

On the other hand, in the case that the sensor 112B has not detected attaching of the panel 10B (S10: No), it is preferable that the controller 116B do not advance the process to a next step, and it prevent activation of the inhaler 100B. That is, it is preferable that the inhaler 100B keep a state wherein a user is not allowed to power it up. This is because manipulation for pressing the manipulation button 24B in the state that the panel 10B is not attached to the main-body housing 20B cannot be regarded as normal manipulation, and the possibility that the above manipulation is erroneous manipulation is high. Since such manipulation may be regarded as inappropriate manipulation when safety is taken into consideration, the manipulation for pressing the manipulation button 24B should not be allowed. Thus, in such a case, operation for supplying electric power from the electric power supply 111B to the heater 121B can be inhibited.

It is preferable to judge, by using the data measured in S20, whether attaching of the panel 10B to the main-body housing 20B is appropriately completed (this is not shown in the figure). For example, it is preferable to judge that the state of attaching is appropriate, if the quantity of magnetic force detected in S10 is equal to or greater than a predetermined threshold value or within a predetermined range of values. On the other hand, it is preferable to judge that the state of attaching is inappropriate, if the quantity of magnetic force is less than a predetermined threshold value or out of a predetermined range of values. Further, in the case that the state of attaching of the panel 10B to the main-body housing 20B is judged to be inappropriate, it is also preferable to inhibit supplying of electric power from the electric power supply 111B to the heater 121B, for safety. By the above construction, safety with respect to the inhaler 100B can be improved.

Next, the controller 116B specifies an operation profile associated with the data measured in S20 (S30). Plural operation profiles are stored in advance in the memory 114B, and the respective operation profiles are associated, in advance, with the respective quantities of magnetic force that are to be detected. For example, a first operation profile is specified if magnetic force having a value in a range from 3.5 kG to 3.7 kG is detected in S20, and so on. In an embodiment, it is constructed in such a manner that the quantities of magnetic force are different from one another according to the types of the panels 10B, respectively. Further, the operation profile, which is to be specified, comprises a heating profile of the heater 121B (this will be explained later).

Thereafter, the controller 116B makes the sensor 112B detect whether the opening 142 is being opened by the shutter 50 (S40). In the case that the opening 142 is being opened by the shutter 50, a user is allowed to insert the stick-type base material 150 into the columnar inner space 141 via the opening 142, and make the holding part 140 hold it.

After insertion of the stick-type base material 150, the controller 116B makes the sensor 112B detect pressing of the manipulation button 24B (S50), in response to pressing of the manipulation button (22A and 24B) via the panel 10B that is result of pressing of the panel 10B by fingers of a user. As a result, the inhaler 100B is activated, and the state thereof is changed to a powered-up state wherein electric power supply is being turned on. In this regard, as explained above, even if the manipulation button 24B is pressed, the above manipulation is not accepted in view of prevention of erroneous operation if the panel 10B is not being attached to the main-body housing 20B. That is, operation for supplying electric power from the electric power supply 111B to the heater 121B is still inhibited and is not allowable.

In response to changing of the state of the inhaler 100B to the powered-up state, the controller 116B makes the electric power supply 111B start supplying of electric power to the heater 121B (S60). Pressing of the manipulation button 24B by a user in step S50 may be used as a trigger to execute S60. In a different construction, detection, by the sensor 112B, of a first time suction action (puff action) performed by a user may be used as a trigger to execute S60.

Following the above process, the controller 116B makes the inhaler 100B perform operation based on the operation profile specified in S30. (S70). In an embodiment, operation of the inhaler 100B is controlled based on the specific heating profile that will be explained below.

Figure 6:
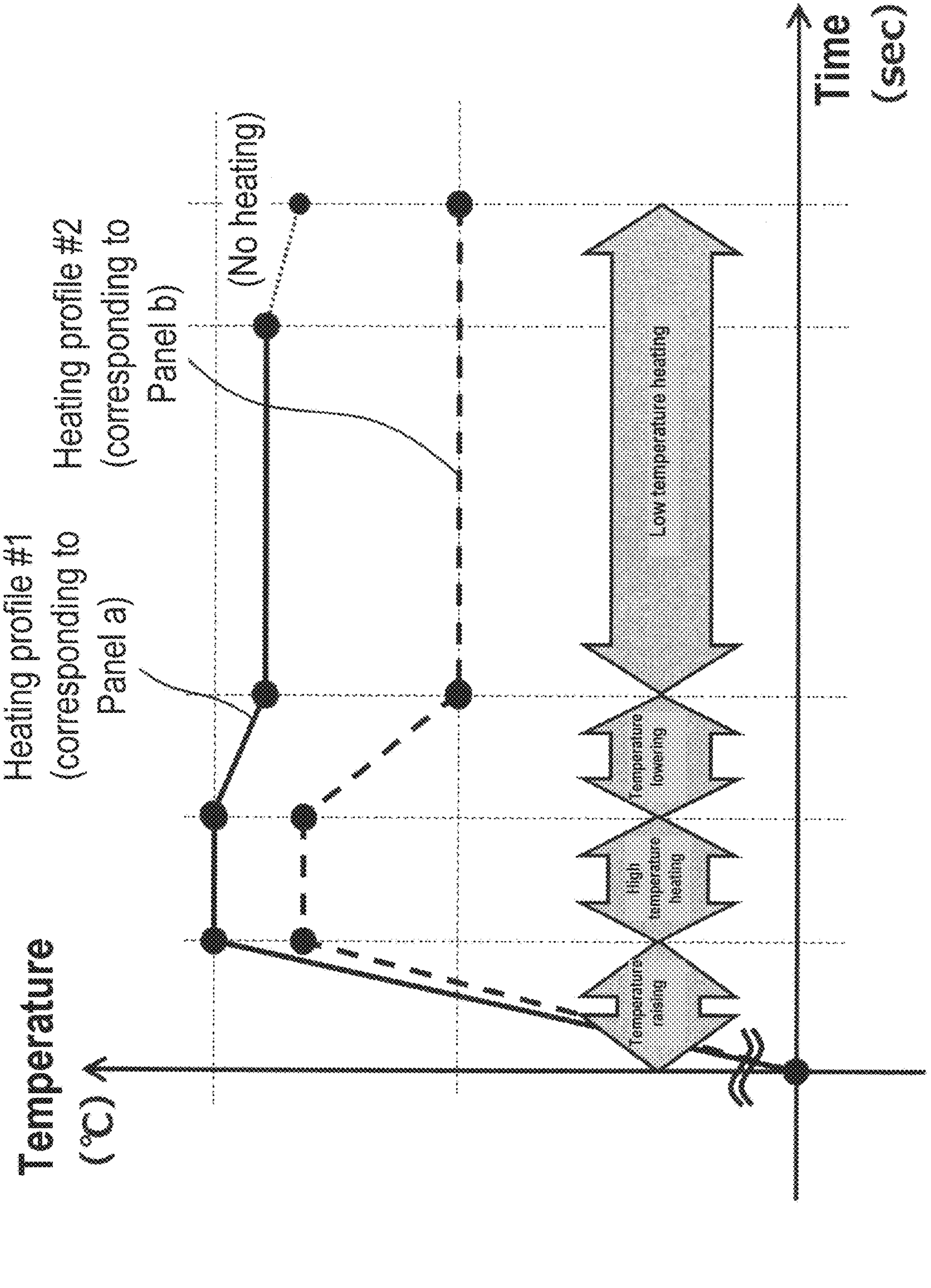
FIG. 6 is a graph which shows temperature transition based on an example hearting profile.

FIG. 6 is a graph which shows temperature transition of the heater 121B in the inhaler 100B, based on plural hearting profiles stored in the memory 114B. In the graph, the vertical axis represents temperature (Celsius, C.°) and the horizontal axis represents time (seconds). In the present case, examples of two heating profiles #1 and #2 are shown in the graph, and either one of the heating profiles is selected based on the data measured in relation to the panel 10B. The heating profiles #1 and #2 are mere examples, and the heating profiles are not limited to them.

Each of the heating profiles #1 and #2 is defined by a temperature raising step, a high-temperature heating step, a temperature lowering step, and a low-temperature heating step. Especially, the temperature during the high-temperature heating step (the highest temperature) is high, so that the operation of the inhaler 100B makes a user experience strong taste/flavor during suction action. On the other hand, the temperature in the heating profile #2 is defined to be that lower than the temperature in the heating profile #1, and, especially, the temperature during the low-temperature heating step (the lowest temperature) is low; however, since the duration of the low-temperature heating step thereof is longer than that in the heating profile #1, a user can perform suction action for a long period of time while experiencing light taste/flavor during the suction action.

In an embodiment, it is constructed in such a manner that respective heating profiles, that are different from one another, are set according to the respective types of an attached panel 10B, that are different from one another. For example, the respective panel types and the respective heating profiles are associated with one another, for example, in such a manner that operation using the heating profile #1 is performed when the panel type is "Panel a for male" and operation using the heating profile #2 is performed when the panel type is "Panel b for female."

That is, in an embodiment, in the operation of the inhaler 100B, as a result that a user simply attaches the panel 10B thereto, a heating profile corresponding to a panel is automatically set. That is, a user is not required to grasp predetermined manipulation for setting of operation of the inhaler 100B, and to perform the setting manipulation every time when powering up the inhaler 100B. By the above construction, usability of the inhaler 100B can be improved, and a user's feeling of satisfaction with respect to the inhaler 100B can be improved.

Further, in general, it is assumed that setting that a user, who uses an inhaler, prefers is uniquely determined mostly. This is because it is considered that user's preference with respect to smoke flavor and so on does not change much during a period of time that a user possesses an inhaler. That is, according to the construction of the inhaler 100 according to an embodiment, by simply attaching a panel 10B, which has setting contents corresponding to user's preference, to the main-body housing 20B, the setting contents can be maintained as default setting contents with respect to the inhaler 100B during the period that the above attaching state is maintained. By the above construction, various kinds of burdens on a user, that relate to manipulation required to be performed by a user for setting the inhaler 100B, can be reduced, and a user's feeling of satisfaction with respect to the inhaler 100B can be improved. In this regard, it is preferable to adopt a construct such that the setting contents of the inhaler 100B, that are associated with the attached panel 10B, are further changeable later via user's predetermined input manipulation.

5. MODIFICATION EXAMPLES

(1) Modification Example 1 Relating to Construction of Inhaler

In the above explanation relating to the inhaler, it is explained that a magnetic sensor (23A and 22B) is installed in the main-body housing 20, and a magnetic field from the magnetic field applicator (the magnet 13A and the magnetic substance 13B) constructed in the panel 10 is detected. In the present modification example, the sensor is not limited to such a magnetic sensor, and, for example, a reflection-type photosensor comprising a pair of a light emitting element and a light receiving element may be used. Specifically, it may be possible to adopt a construction such that a reflection-type photosensor is installed in the main-body housing 20, and light from a light emitting element is reflected by the panel 10 and the reflected light is detected by a light receiving element.

(2) Modification Example 2 Relating to Operation of Inhaler

In the above explanation relating to the inhaler, it is explained that, in the case that attaching of the panel 10B is not detected in S10 (No), the controller 116B does not allow proceeding of the process to a next step, and does not allow powering up of the inhaler 100B, accordingly. That is, the inhaler 100B is brought to a state wherein a user is not allowed to power it up.

In the present modification example, in addition to the above construction, or in place of the above construction, it is possible to adopt a construction such that the operation mode of the inhaler 100B is not changeable. The operation modes of the inhaler 100B comprise an error mode at the time of abnormal operation, a sleep mode that automatically starts when operation is not performed for a predetermined period of time, and a normal operation mode during that normal operation, such as starting of heating (S60), wireless communication, and so on, can be performed. That is, in the case that attaching of the panel 10B is not detected in S10, mode transition between the above modes is inhibited.

The construction, such as that explained above, of the inhaler 100B is made based on a point of view of safety, mainly. It is required that the inhaler 100B be constructed in such a manner that the heat generated by the heater 121B does not leak to the outside of the inhaler 100B. In the inhaler 100B according to an embodiment, it is also necessary to take safety into consideration as much as possible, for preventing, at least, a user from getting burned or the like due to heat leaked to the outside of the panel 10B.

(3) Modification Example 3-1 Relating to Operation of Inhaler

In the above explanation that relates to the operation of the inhaler 100B and also relates to the above modification example 1 relating to the operation of the above inhaler 100B, it is explained that, in response to changing of the state of the inhaler 100B to the powering-up state S60 on the assumption that the panel 10B has been detected in S10, the controller 116B makes the electric power supply 111B start supplying of electric power to the heater 121B in S70. That is, until the panel 10B is detected, the inhaler 100B does not change the state to the powering-up state, and is not allowed (i.e., is inhibited) to perform operation for supplying electric power from the electric power supply 111B to the heater 121B.

In the present modification example, the condition to allow supplying of electric power from the electric power supply 111B to the heater 121B is not limited to that explained above. Specifically, it is possible to adopt a construction such that the controller 116B allows supplying of electric power from the electric power supply 111B to the heater 121B, in the case that the value of data measured by the sensor 112B is that in a predetermined range and the manipulation button (22A and 24B) is pressed via action for pressing the panel 10B. For example, it is preferable to adopt a construction such that supplying of electric power is allowed, if the manipulation button (22A and 24B) is pressed via the panel 10B when the magnitude of the magnetic force detected by the magnetic sensor (23A and 22B) is that within the range between 3.5 kG and 5.0 kG. On the other hand, supplying of electric power is still not allowed, if the magnitude of the magnetic force is not that within the range between 3.5 kG and 5.0 kG.

By the above construction, it becomes possible to exclude imitated panel-use action performed by a third person. Further, it becomes possible to appropriately limit use of a panel which has a deteriorated magnet, so that safety of the inhaler can be improved. Further, even in the case that an object having magnetic force is accidentally positioned close to the main-body housing in a user's bag or the like, erroneous operation of the inhaler can be prevented by defining the predetermined range in advance, and this is also advantageous in terms of conservation of electric power.

(4) Modification Example 3-2 Relating to Operation of Inhaler

In place of the above construction, it is possible to adopt a construction such that the controller 116B allows supplying of electric power from the electric power supply 111B to the heater 121B, in the case that both the state that the panel 10B is being attached to the main-body housing 20B in S20 and the state that the opening 142 is being opened by the shutter 50 in S40 are detected by the sensor 112B. By the above construction, safety of the inhaler can be improved.

(5) Modification Example 4 Relating to Operation of Inhaler

In the above explanation relating to operation of the inhaler 100B, it is explained that an operation profile (especially, a heating profile of the inhaler 100B) is specified in S30, based on data measured by the sensor 112B in S20. In the present modification example, in addition to the above construction, the controller 116B may control operation of the communicator 115B in such a manner that operation of the communicator 115B is enabled or disabled according to the data measured by the sensor 112B in S20.

Regarding the inhaler 100B, updating of various kinds of setting information and/or firmware relating to the inhaler 100B stored in the memory 114B can be performed via wireless communication by the communicator 115B with an external device. Further, user information and/or user's inhalation information can be communicated between it and an external device. Especially, it is preferable to construct the inhaler 100B in such a manner that the control mode of the notifier 113B (light emission, vocalization, vibration, etc.) and information relating to part of a heating profile at the time of suction (the range of temperature allowed during heating, the length of time of heating, the number of times of suction actions, etc.), for example, be rewritable based on an instruction from an external device connected via the communicator 115B.

It is preferable that the operation of the wireless communication of the communicator 115B be constructed in such a manner that it is enabled or disabled by button manipulation applied to the inhaler 100B. For example, especially, there is a risk that electric power is consumed uselessly, if the wireless communication operation is enabled as a result of erroneous manipulation by a user. In view of the above matter, it is preferable to construct the controller 116B, for example, in such a manner that heating operation in accordance with the heating profile #1, that corresponds to the panel type "Panel a for male," is performed if the type of the attached panel is "Panel a for male," and at the same time, the wireless communication operation of the communicator 115B is disabled. On the other hand, it is preferable to construct it in such a manner that heating operation in accordance with the heating profile #2, that corresponds to the panel type "Panel b for female," is performed if the type of the attached panel is "Panel b for female," and at the same time, the wireless communication operation of the communicator 115B is enabled. By the above construction, it becomes possible to prevent useless consumption of electric power due to erroneous manipulation of a button by a user or the like.

(6) Modification Example 5 Relating to Operation of Inhaler

In the above explanation relating to operation of the inhaler 100B, it is explained that an operation profile is specified in S30, and the inhaler 100B is operated based on the operation profile in S70. The above operation profile is that relating to a heating profile for the heater 121B. In the present modification example, in addition to the above construction, or in place of the above construction, the operation profile may comprise a light emission profile for the notifier 113B comprising a single LED or plural LEDs.

Specifically, it is preferable that the controller 116B specify, in S30, as an operation profile, a light emission profile relating to one or more of the color of light emitted from an LED, the cycle of light emission, and the pattern of light emission (emitting red light and blue light alternatingly, or the like). Further, it is preferable to construct the controller 116B in such a manner that it operates the inhaler 100B, in S70, based on a specified light emission profile(s) in relation to at least one of a period of time during that inhaled components are being generated and a period of time during that inhaled components are not being generated in the inhaler 100B. By the above construction, various kinds of burdens on a user, that relate to manipulation required to be performed by a user for setting the inhaler 100B, can be reduced, and a user's feeling of satisfaction with respect to the inhaler 100B can be improved.

(7) Modification Example 6-1 Relating to Operation of Inhaler

In the above explanation relating to operation of the inhaler 100B, it is explained that the controller 116B makes the electric power supply 111B start supplying of electric power to the heater 121B in S60, and makes the inhaler 100B operate based on the operation profile in S70.

In the present modification example, in addition to the above construction, the controller 116B may be constructed to stop operation for supplying electric power, in the case that it becomes unable to measure data by the sensor 112B during a period when supplying of electric power from the electric power supply 111B to the heater 121B is being performed in S70. Specifically, there are two cases assumed, i.e., the case wherein the sensor 112B becomes unable to measure data and the case wherein the panel 10B is detached from the main-body housing 20B during heating. That is, supplying of electric power should be stopped forcibly in view of safety. Further, it is also preferable that the controller 116B work to disable communication function of the communicator 115B forcibly, in the case that data communication with an external device via the communicator 115A is being performed. By the above construction, safety of the inhaler 100B can be further improved.

(8) Modification Example 6-2 Relating to Operation of Inhaler

In addition to the above construction, the controller 116B may be constructed in such a manner that it stops operation for supplying electric power, in the case that the sensor 112B has detected closing of the opening 142 by the shutter 50 during a period when supplying of electric power from the electric power supply 111B to the heater 121B is being performed in S70. This is because manipulation of the shutter 50 during a period when electric power is being supplied is not usually expected. By the above construction, safety of the inhaler 100B can be further improved.

Other Embodiments

In the above description, inhalers and methods according to some embodiments have been explained with reference to the figures. It will be understood that the present disclosure can be implemented as a program for making a processor execute the method for operating the inhaler when the program is executed by the processor, or a computer-readable storage medium storing the program.

In the above description, embodiments of the present disclosure have been explained together with their modification examples and application modes; and, in this regard, it should be understood that they are mere examples, and they are not those limiting the scope of the present disclosure. It should be understood that change, addition, modification, and so on with respect to the embodiments can be performed appropriately, without departing from the gist and the scope of the present disclosure. The scope of the present disclosure should not be limited by any of the above-explained embodiments, and should be defined by the claims and equivalents thereof only.

REFERENCE SIGNS LIST

10, 10A, 10B . . . Panel: 11A, 13A, 14A, 15B, 21A, 21B, 24A, 25B . . . Magnet: 11B . . . Base: 12B . . . Leg: 12A, 14B . . . Projection: 13B . . . Magnetic substance: 18 . . . Indicator: 20, 20A, 20B . . . Main-body housing: 22A, 24B . . . Manipulation button: 22B, 23A . . . Magnetic sensor: 25A, 23B . . . Indicator window: 26A, 26B . . . Magnetic force detecting area: 30 . . . Main body: 40 . . . Housing: 50 . . . Shutter: 100 (100A, 100B) . . . Inhaler: 110 . . . Electric power source unit: 111A, 111B . . . Electric power supply: 112A, 112B . . . Sensor: 113A, 113B . . . Notifier: 114A, 114B . . . Memory: 115A, 115B . . . Communicator: 116A, 116B . . . Controller: 120 . . . Cartridge: 121A, 121B . . . Heater: 122 . . . Liquid guide: 123 . . . Liquid reservoir: 124 . . . Mouthpiece: 130 . . . Flavor-adding cartridge: 131 . . . Flavor source: 140 . . . Holding part: 141 . . . Inner space: 142 . . . Opening: 143 . . . Bottom part: 144 . . . Heat insulator: 150 . . . Stick-type base material: 151 . . . Base material part: 152 . . . Suction opening part: 180 . . . Air flow path: 181, 191 . . . Air inflow hole: 182, 192 . . . Air outflow hole

The invention claimed is:

1. An inhaler, which comprises a first member and a second member which is constructed to be attachable/detachable to/from the first member, comprising:

an active functional part constructed in the first member;

a passive functional part which is constructed in the second member, and changes its state in response to an effect applied by the active functional part;

a sensor which is installed in the first member, and detects a state, that is changed, of the passive functional part; and a controller which judges, based on the detected state, attaching of the second member to the first member, wherein the passive functional part in the second member is positioned to be aligned with both the active functional part and the sensor when the second member is attached to the first member, the passive functional part comprises a base and a leg extending from the base, and the base is aligned with the active functional part and the leg is aligned with the sensor when the second member is attached to the first member, and wherein the active functional part in the first member is positioned to be separated from the sensor; and the separated distance is larger than a distance between the passive functional part and the sensor in a state that the second member is being attached to the first member.

2. The inhaler as recited in claim 1, wherein the active functional part comprises a permanent magnet for generating a first magnetic field;

the passive functional part comprises a magnetic substance which is magnetized by the first magnetic field for generating a second magnetic field; and the sensor comprises a magnetic sensor for detecting magnetic force that is based on the second magnetic field.

3. The inhaler as recited in claim 2, wherein the magnetic substance in the passive functional part comprises a ferromagnet or a paramagnet.

4. The inhaler as recited in claim 1, wherein the second member is constructed to be held by the first member by plural holding structures; and at least one of the plural holding structures comprises the active functional part and the passive functional part.

5. The inhaler as recited in claim 4, wherein the at least one of the plural holding structures is constructed to hold the second member attached to the first member by magnetic attraction between the active functional part and the passive functional part.

6. The inhaler as recited in claim 1, wherein the sensor detects the state of the leg.

7. The inhaler as recited in claim 1, wherein the separated distance is larger than the distance between the leg and the sensor in the state that the second member is being attached to the first member.

8. The inhaler as recited in claim 1, wherein the first member comprises a manipulation button on a surface to which the second member is attached; and the manipulation button is covered by the second member when the second member is attached to the first member.

9. The inhaler as recited in claim 8 further comprising a heater for heating an inhaled component source for generating inhaled components; wherein the inhaler is constructed to allow supplying of electric power to the heater when the manipulation button is pressed via the second member.

* * * * *